US007361805B2

(12) United States Patent
Yano et al.

(10) Patent No.: US 7,361,805 B2
(45) Date of Patent: Apr. 22, 2008

(54) EHD1 GENE PROMOTING PLANT FLOWERING, AND UTILIZATION THEREOF

(75) Inventors: Masahiro Yano, Ibaraki (JP); Takuichi Fuse, Miyazaki (JP); Utako Yamanouchi, Ibaraki (JP); Atsushi Yoshimura, Fukuoka (JP); Kazuyuki Doi, Fukuoka (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 196 days.

(21) Appl. No.: 10/515,481

(22) PCT Filed: May 20, 2003

(86) PCT No.: PCT/JP03/06273

§ 371 (c)(1),
(2), (4) Date: Jun. 6, 2005

(87) PCT Pub. No.: WO03/100062

PCT Pub. Date: Dec. 4, 2003

(65) Prior Publication Data

US 2005/0257292 A1    Nov. 17, 2005

(30) Foreign Application Priority Data

May 28, 2002   (JP) ............................. 2002-153807

(51) Int. Cl.
*C12N 15/29* (2006.01)
*C12N 15/82* (2006.01)
*C12N 5/04* (2006.01)
*A01H 5/00* (2006.01)

(52) U.S. Cl. ...................... 800/278; 800/298; 800/290; 800/320.2; 435/320.1; 435/419; 536/23.6

(58) Field of Classification Search ............... 536/23.1, 536/23.6; 435/320.1, 410; 800/298, 278, 800/290, 320.2
See application file for complete search history.

(56) References Cited

U.S. PATENT DOCUMENTS

| | | | | |
|---|---|---|---|---|
| 6,225,530 | B1* | 5/2001 | Weigel et al. ............... | 800/290 |
| 6,359,198 | B1* | 3/2002 | Strabala et al. ............. | 800/298 |
| 2003/0233670 | A1* | 12/2003 | Edgerton et al. ........... | 800/278 |

FOREIGN PATENT DOCUMENTS

| | | |
|---|---|---|
| JP | 04/89036 A | 3/2004 |
| JP | 04/290190 A | 10/2004 |
| WO | WO 01/32880 A1 | 5/2001 |
| WO | WO 01/32881 A1 | 5/2001 |
| WO | WO 02/42475 A1 | 5/2002 |

OTHER PUBLICATIONS

Bowie et al, Science 247:1306-1310, 1990.*
McConnell et al, Nature 411 (6838):709-713, 2001.*
MacDonald et al (2003, Cell 113:671-672).*
Buell et al (2001, NCBI Accession No. AC027038).*
An unverified English language translation of document AL1, WO 01/32880 A1.
An unverified English language translation of document AM1, WO 01/32881 A1.
An unverified English language translation of document AN1, WO 02/42475 A1.
An unverified English language translation of document AO1, JP 04/290190 A.
An unverified English language translation of document AP1, JP 04/89036 A.
Doi, K., et al., "RFLP Mapping and QTL Analysis of Heading Date and Pollen Sterility Using Backcross Populations between *Oryza sativa* L. and *Oryza glaberrima* Steud.," *Breeding Science* 48:395-399, Japanese Society of Breeding (1998).
Doi, K., et al., "Construction and evaluation of *Oryza glaberrima* Steud. Chromosome substition lines of rice.—RFLP mapping of loci for heading date and hybrid sterility located on chromosome 10," *Breeding Science* 48(separate vol. 2):104, Japanese Society of Breeding (1998).
Izawa, T., et al., "Comparative biology comes into bloom: genomic and genetic comparison of flowering pathways in rice and *Arabidopsis*," *Curr. Opin. Plant Biol.* 6:113-120, Elsevier Science Ltd. (Apr. 2003).
Kojima, S., et al., "*Hd3a*, a Rice Ortholog of the *Arabidopsis FT* Gene, Promotes Transition to Flowering Downstream of *Hd1* under Short-Day Conditions," *Plant Cell Physiol.* 43:1096-1105, Oxford University Press (Oct. 2002).
Takahashi, Y., et al., "*Hd6*, a rice quantitative trait locus involved in photoperiod sensitivity, encodes the α subunit of protein kinase CK2," *Proc. Natl. Acad. Sci. USA* 98:7922-7927, National Academy of Sciences (2001).
Yano, M., et al., "Genetic Control of Flowering Time in Rice, a Short-Day Plant," *Plant Physiol.* 127:1425-1429, American Society of Plant Biologists (Dec. 2001).
Yano, M., et al., "*Hd1*, a Major Photoperiod Sensitivity Quantitative Trait Locus in Rice, Is Closely Related to the *Arabidopsis* Flowering Time Gene *CONSTANS*," *The Plant Cell* 12:2473-2483, American Society of Plant Physiologists (2000).
Yano, M., et al., "Ine-Genome Kozo to Kino Kaimei no Saisentan," *Kagaku to Seibutsu* 41:42-47, Gakkai Syuppan Center Press (Jan. 2003).
Kang, H.-G., "Characterization of Two Rice MADS Box Genes That Control Flowering Time," *Mol. Cells* 7:559-566, The Korean Society for Molecular Biology (1997).
EMBL Accession No. AC027038 (Sep. 2002).
Nishida, H. et al., "Analysis of Tester Lines for Rice (*Oryza sativa* L.) Heading-time Genes Using Reciprocal Photoperiodic Transfer Treatments," *Ann. Botany* 88:527, Annals of Botany Company (2001).

* cited by examiner

*Primary Examiner*—Stuart F. Baum
(74) *Attorney, Agent, or Firm*—Sterne, Kessler, Goldstein & Fox P.L.L.C.

(57) ABSTRACT

A detailed linkage analysis of the Ehd1 region was performed with a large segregating population, essential for map-based cloning. As a result, the Ehd1 gene promoting rice heading (flowering) was successfully isolated. Rice heading time was also found to be altered upon introduction of this gene. Based on these facts, the newly isolated and identified Ehd1 gene is expected to be useful in promoting plant flowering.

16 Claims, 8 Drawing Sheets

FIG. 7

```
                  ****************************************************************************************
Taichu 65      1  MDHRELWPYGLRVLVIDDDCSYLSVMEDLLLKCSYKVTTYKNVREAVPFILDNPQIVDLVISDAFFPTEDGLLILQEVTSKFGIPTVIMA   90
Nipponbare     1  MDHRELWPYGLRVLVIDDDCSYLSVMEDLLLKCSYKVTTYKNVREAVPFILDNPQIVDLVISDAFFPTEDGLLILQEVTSKFGIPTVIMA   90
Kasalath       1  MDHRELWPYGLRVLVIDDDCSYLSVMEDLLLKCSYKVTTYKNVREAVPFILDNPQIVDLVISDAFFPTEDGLLILQEVTSKFGIPTVIMA   90
IRGC104038     1  MDHRELWPYGLRVLVIDDDCSYLSVMEDLLLKCSYKVTTYKNVREAVPFILDNPQIVDLVISDAFFPTEDGLLILQEVTSKFGIPTVIMA   90

*************** ******* **************************** ****** ******************************
Taichu 65     91  SSGDTNTVMKYVANGAFDFLLKPVRIEELSNIWQHIFRKQMQDHKNNNMVGNLEKPGHPPSILAMARATPATTRSTATEASLAPLENEVR  180
Nipponbare    91  SSGDTNTVMKYVANGAFDFLLKPVRIEELSNIWQHIFRKQMQDHKNNNMVGNLEKPGHPPSILAMARATPATTRSTATEASLAPLENEVR  180
Kasalath      91  SSGDTNTVMKYVANGAFDFLLKPVRIEELSNIWQHIFRKQMQDHKNNNMVGNLEKPGHPPSILAMARATPATTRSTATEASLAPLENEVR  180
IRGC104038    91  SSGDTNTVMKYVANGASDFLLKPVRIEELSNIWQHIFRKQMQDHKNNNMVGNLEKPGHPPSILAMARATPATTKSTATEALLAPLENEVR  180

****************  ****** **********************************************************
Taichu 65    181  DDMVNYNGEITDIRDLGKSRLTWTTQLHRQFIAAVNHLREDKAVPKKILGIMKVKHLTREQVASHLQKYRMQLKKSIPTTSKHGATLSST  270
Nipponbare   181  DDMVNYNGEITDIRDLGKSRLTWTTQLHRQFIAAVNHLGEDKAVPKKILGIMKVKHLTREQVASHLQKYRMQLKKSIPTTSKHGATLSST  270
Kasalath     181  DDMVNYNGEITDIRDLGKSRLTWTTQLHRQFIAAVNHLGEDKAVPKKILGIMKVKHLTREQVASHLQKYRMQLKKSIPTTSKHGATLSST  270
IRGC104038   181  DDMVNYNGEITDIRDLRKSRLTWTTQLHRQFIAAVNHLGEDKAVPKKILGIMKVKHLTREQVASHLQKYRMQLKKSIPTTSKHGATLSST  270

****************** ************* ************************
Taichu 65    271  ALDKTQDHPSRSQYFNQDGCKEIMDYSLPRDDLSSGSECMLEELNDYSSEGFQDFRWDSDKQEYGPCFWNF  341
Nipponbare   271  ALDKTQDHPSRSQYFNQDGCKEIMDYSLPRDDLSSGSECMLEELNDYSSEGFQDFRWDSDKQEYGPCFWNF  341
Kasalath     271  ALDKTQDHPSRSQYFNQDGCMEIMDYSLPRDDLSSGSECMLEELNDYSSEGFQDFRWDSDKQEYGPCFWNF  341
IRGC104038   271  ALDKTQDHPSRSQYFNQDGCMEIMDYSLPRDDLSSGSECMLEEQNDYSSEGFQDFRWDSDKQEYGPCFWNF  341
```

EHD1 GENE PROMOTING PLANT FLOWERING, AND UTILIZATION THEREOF

TECHNICAL FIELD

The present invention relates to Ehd1 genes that promote plant flowering, and utilization thereof.

BACKGROUND ART

Rice heading time (flowering time) is mainly determined by photoperiod sensitivity that depends on day length and other factors (basal vegetative growth or temperature sensitivity). Genetic analysis of heading time has been performed for some time, and to date, heading time-associated genes such as Se1 locus (chromosome 6), E1 locus (chromosome 7), E2 locus (unknown), E3 locus (chromosome 3), or Ef1 locus (chromosome 10) (Kinoshita, Rice Genetics Newsletter 15: 13-74, 1998; Nishida et al., Ann. Bot. 88: 527-536, 2001) have been discovered using mutations and variations inherent to rice cultivars. Recently, the use of DNA markers in rice genetic analyses has advanced the genetic analysis of characteristics such as heading time that exhibits complex inheritance (quantitative traits) (Yano et al., Plant Physiol. 127: 1425-1429, 2001). Genes associated with rice photoperiod sensitivity have been isolated based on this work (Yano et al., Plant Cell 12: 2473-2484, 2000; Takahashi et al., PNAS 98: 7922-7927, 2001; Kojima et al., Plant Cell Physiol. 43: 1096-1105, 2002; Yano, Curr. Opin. Plant Biol. 4: 130-135, 2001). Attempts to use these isolated rice-heading-time-associated genes to elucidate genetic control mechanisms are also progressing (Izawa et al., Gene Dev. 16: 2006-2020, 2002; Hayama et al., Nature 422: 719-722, 2003). On the other hand, many cases of isolation of genes associated with plant flowering have been reported in *Arabidopsis thaliana* (Simpson, G. G. and Dean, C., Science 296: 285-289 (2002); Mouradov, A. et al., Plant Cell (Suppl.) 14: S111-130 (2002)). Furthermore, methods for controlling flowering time in *Arabidopsis thaliana* (a plant) using these genes have been proposed (Published Japanese Translation of International Publication Nos.: 2002-511270; 2002-532069; 2002-537768; 2000-512845; Hei 11-512289; Hei 11-506001; and Hei 10-508481). At the same time, a method for using rice genes to alter the flowering time of *Arabidopsis thaliana* (a plant) has also been suggested (Published Japanese Translation of International Publication No. 2002-335970). However, a great number of the genes associated with rice heading time remain to be isolated.

DISCLOSURE OF THE INVENTION

The present invention was made under these circumstances. An objective of the present invention is to provide novel genes that regulate plant flowering. Another objective of this invention is to modify plant flowering time using these genes.

The Ehd1 locus is a quantitative trait locus (QTL) associated with heading time. It was detected using the progeny of a cross between *japonica* rice cultivar "Taichung 65" and West African region rice cultivar "O. glaberrima Steud." (IRGC 104038). The Ehd1 locus has been proven to be located on the long arm of chromosome 10. Furthermore, analysis using a nearly isogenic line of the Ehd1 region (the IRGC 104038 allele), which comprises a "Taichung 65" genetic background, proved that the Ehd1 locus is associated with heading promotion. Genetic studies hitherto have also proved that the Ehd1 locus was mapped as a single Mendelian locus (formally called Ef(t)) in the interval between RFLP markers C234 and G37, and co-segregated with C1369. However, isolating genes using map-based cloning was difficult at the level of resolution of this linkage analysis.

The present inventors carried out a detailed linkage analysis of the Ehd1 region with a large segregating population essential for map-based cloning. A generation of progenies derived from backcrossing Taichung 65 and IRGC 104038 was used as the segregating population for linkage analysis. From these backcrossed progenies, those whose Ehd1 region was heterologous, and whose other genomic regions were mostly substituted with the Taichung 65 type genome were selected. From the 2500 progeny plants (F2 generation) produced by these selected plants by self-fertilization, plant having a chromosome with a recombination near the Ehd1 locus were selected using CAPS markers C1286 and G37, which flank the Ehd1. Genotype of Ehd1 locus was determined by a progeny test of the F3 generation. As a result of linkage analysis, it was demonstrated that the Ehd1 was mapped between RFLP markers C814A and C234, and identified eight recombinant plants for C814A and two recombinant plants for C234.

Since the nucleotide sequences of the RFLP markers flanking the Ehd1 gene were found to be included in the published genomic nucleotide sequence information, the nucleotide sequence of the Ehd1 candidate genomic region was obtained from the published nucleotide sequence data. Using information on the nucleotide sequence of the candidate genomic region, novel CAPS markers were created to narrow down the candidate gene region. As a result, the Ehd1 candidate region was proved to be about 16 kb, flanked by CAPS markers 26-28 and 12-14. Gene predictions and similarity searches were carried out against the nucleotide sequence of this candidate region proved the presence of three types of predicted genes. One type showed similarity to the two-component response regulator (ARR) gene of *Arabidopsis*. The other two types of predicted genes were highly similar to rice EST, but shared no similarity to known genes with established functions. However, since none of these predicted genes could be excluded as Ehd1 candidates, these three types of predicted genes were transformed to verify function as Ehd1 candidates.

For transformation, a BAC library was constructed from genomic DNAs derived from the indica rice cultivar Kasalath assumed to comprise a functional Ehd1 allele. A BAC clone KBM128G10 comprising the Ehd1 candidate gene was selected for use from the library. From the BAC clone KBM128G10, an 11.5 kb BamHI fragment comprising the ARR-like candidate gene and one of the predicted genes having a high similarity to the rice EST, and a 7.6 kb KpnI fragment comprising two predicted genes other than the ARR-like candidate gene, were excised. Each of these fragments was incorporated into a Ti-plasmid vector pPZP2H-lac, and introduced into Taichung 65 via *Agrobacterium*. Regenerated plants were immediately transferred into growth chambers and cultivated under short-day conditions to measure the number of days until their heading. Almost all of the transgenic plants ($T_0$) that were introduced with the 11.5 kb BamHI fragment headed earlier than those with the vector alone. On the other hand, the number of days to heading in plants introduced with the 7.6 kb KpnI fragment was about the same as for plants with the vector alone. Furthermore, transcription of the ARR-like Kasalath-derived candidate gene was observed in almost all of the plants introduced with the 11.5 kb BamHI fragment. From these results the Ehd1 candidates could thus be narrowed down to the ARR-like candidate gene comprised in the 11.5 kb BamHI fragment.

Furthermore, to confirm that heading promotion was due to the transgene, plants with lower copy numbers of the gene were selected from those transgenic plants ($T_0$) with earlier heading. The inbred progenies thereof were cultivated under short-day conditions to investigate the number of days until heading. Each of the three types of progeny populations were respectively divided into early-maturing plants and late-maturing plants. All the early-maturing plants retained the transformed Kasalath-derived ARR-like candidate gene, and the number of days to their heading was essentially the same as for the nearly isogenic line, T65(Ehd1), in which the Ehd1 region of Taichung 65 had been substituted with the Ehd1 gene of *O. glaberrima*. On the other hand, the number of days to Taichung 65 heading was the same as that of late-maturing plants. These results proved that the ARR-like candidate gene was the Ehd1 gene.

In rice cultivars *O. glaberrima* (IRGC 104038), Kasalath, Nipponbare, and Taichung 65, genomic nucleotide sequences of about 7.6 kb in their Ehd1 regions were analyzed to compare the amino acid sequences of their respective predicted translational products. It was revealed that seven amino acids were substituted between IRGC 104038 and Taichung 65, two between Kasalath and Taichung 65, and one between Nipponbare and Taichung 65. Of these, the substitution of the $219^{th}$ amino acid glycine to arginine was a unique mutation occurring only in Taichung 65. This glycine was highly conserved among the known ARR gene family. This amino acid mutation was thus assumed to be associated with the reduced Ehd1 function of Taichung 65-derived plants.

Therefore, it is expected that the newly isolated Ehd1 gene can be utilized to promote plant flowering (heading), and that DNAs which elicit a reduced function of the Ehd1 gene can be used to delay plant flowering.

Namely, the present invention relates to the Ehd1 gene, which promotes plant flowering (heading), and to utilization thereof. More specifically, the present invention provides the following:

[1] A DNA according to any one of the following (a) through (d), wherein said DNA encodes a plant-derived protein comprising a function of promoting plant flowering:

(a) a DNA encoding a protein comprising the amino acid sequence of SEQ ID NO: 3, 6, or 9;

(b) a DNA comprising a coding region of a nucleotide sequence of SEQ ID NO: 1, 2, 4, 5, 7, or 8;

(c) a DNA encoding a protein comprising an amino acid sequence of SEQ ID NO: 3, 6, or 9, wherein one or more amino acids are substituted, deleted, inserted, and/or added; and (d) a DNA hybridizing under stringent conditions with a DNA comprising the nucleotide sequence of SEQ ID NO: 1, 2, 4, 5, 7, or 8;

[2] The DNA of [1], derived from rice;

[3] A DNA according to any one of the following (a) through (d):

(a) a DNA encoding an antisense RNA complementary to the transcriptional product of the DNA of [1] or [2];

(b) a DNA encoding an RNA comprising ribosomal activity that specifically cleaves the transcriptional product of the DNA of [1] or [2];

(c) a DNA encoding an RNA that, due to an RNAi effect, suppresses the expression of the DNA of [1] or [2] upon expression in a plant cell; and (d) a DNA encoding an RNA that, due to a co-suppression effect, suppresses the expression of the DNA of [1] or [2] upon expression in a plant cell;

[4] The DNA of [1] or [2], used to promote plant flowering;

[5] The DNA of [3], used to delay plant flowering;

[6] A vector comprising the DNA of any one of [1] through [5];

[7] A transformed plant cell retaining the DNA of any one of [1] through [5] or the vector of [6];

[8] A transgenic plant comprising the transformed plant cell of [7];

[9] A transgenic plant that is a progeny or a clone of the transgenic plant of [8];

[10] A breeding material of the transgenic plant of [8] or [9];

[11] A method for producing the transgenic plant of [8], comprising the steps of introducing the DNA of any one of [1] through [5] or the vector of [6] into a plant cell, and regenerating a plant from said plant cell;

[12] A method for promoting plant flowering, comprising expressing the DNA of [1] or [2] in plant cells;

[13] A method for delaying plant flowering, comprising suppressing the expression of the endogenous DNA of [1] or [2] in plant cells;

[14] The method of [13], comprising introducing the DNA of [3] into a plant; and

[15] The method of any one of [12] through [14], wherein the plant is rice.

The present invention provides DNAs encoding plant-derived Ehd1 proteins comprising the function of promoting plant flowering.

In this invention, the plants from which DNAs encoding the Ehd1 protein are derived include, but are not limited to, rice, *Arabidopsis thaliana*, soybean, maize, barley, wheat and morning glory, for example.

Furthermore, there is no particular limitation as to the types of plants whose flowering is promoted on transforming the above-described DNA. For example, such plants include useful crops and ornamental plants. Specifically, useful crops include monocotyledons such as rice, and dicotyledons such as soybean. Ornamental plants include flowering plants such as chrysanthemum, morning glory, poinsettia, and cosmos.

In the present invention, "flowering" usually means the blooming of flowers, but refers to heading in gramineous plants such as rice. In this invention, promotion of flowering refers to accelerating flowering time, while delay of flowering refers to delaying flowering time.

Furthermore, the day-length (photoperiod) conditions under which the DNAs of this invention promoted the flowering of the above-described plants are, for example, natural day-length conditions, long-day conditions, short-day conditions, and so on. Short-day conditions are preferred. In this invention, long-day conditions are conditions in which there are 14 or more daylight hours per day. In this example, the light period was set at 15 hours, while the dark period was set at nine hours; however, long-day conditions are not limited to this example. Short-day conditions are those conditions in which there are 11 or fewer daylight hours per day. In this example, the light period was set at ten hours and the dark period at 14 hours; however, short-day conditions are not limited to this example.

Furthermore, in this invention, examples of DNAs encoding Ehd1 proteins are those DNAs comprising the coding region of the nucleotide sequences set forth in SEQ ID NO:

1, 2, 4, 5, 7, or 8, and DNAs encoding proteins comprising the amino acid sequences set forth in SEQ ID NO: 3, 6, or 9.

The present invention also comprises DNAs encoding proteins which are structurally analogous to an Ehd1 protein comprising an amino acid sequence set forth in SEQ ID NO: 3, 6, or 9, and comprising the function of promoting plant flowering.

Whether or not a DNA encodes a protein that comprises the function of promoting plant flowering can be determined by, for example, observing whether or not the flowering of plants introduced with the DNA is promoted; or whether or not the flowering of plants is delayed when they are introduced with a DNA that suppresses the expression of the DNA. Examples of such DNAs include mutants, derivatives, alleles, variants, and homologues that encode proteins comprising an amino acid sequence of SEQ ID NO: 3, 6, or 9, in which one or more of the amino acids are substituted, deleted, added, and/or inserted.

Examples of methods for preparing DNAs that encode proteins comprising altered amino acid sequences are well known to those skilled in the art, and include site-directed mutagenesis (Kramer, W. and Fritz, H.-J., (1987) "Oligonucleotide-directed construction of mutagenesis via gapped duplex DNA." Methods in Enzymology, 154: 350-367). A protein's amino acid sequence may also mutate naturally due to a nucleotide sequence mutation. DNAs encoding proteins comprising an amino acid sequence of an Ehd1 protein wherein one or more amino acids are substituted, deleted, added, and/or inserted are also included in the DNAs encoding Ehd1 proteins of the present invention, so long as they encode a protein functionally equivalent to a naturally occurring type of Ehd1 protein (SEQ ID NO.: 3, 6, or 9). In addition, nucleotide sequence mutations that do not give rise to changes in the amino acid sequence of the protein (degenerate mutations) are also included in the DNAs encoding Ehd1 proteins of the present invention.

DNAs encoding proteins functionally equivalent to Ehd1 proteins, which comprise an amino acid sequence described in SEQ ID NO: 3, 6, or 9, can be produced, for example, by methods well known to those skilled in the art, including hybridization techniques (Southern, E. M. (1975) Journal of Molecular Biology 98: 503.); and polymerase chain reaction (PCR) techniques (Saiki, R. K. et al. (1985) Science 230: 1350-1354; Saiki, R. K. et al. (1988) Science 239: 487-491). That is, it is routine for a person skilled in the art to isolate DNAs with high homology to a DNA encoding Ehd1 protein from rice and other plants, using the genomic sequence of an Ehd1 region (SEQ ID NO: 1, 4, or 7), an Ehd1 cDNA sequence (SEQ ID NO: 2, 5, or 8) or parts thereof as a probe, and oligonucleotides hybridizing specifically to the genomic sequence of the Ehd1 region and the Ehd1 cDNA sequence as a primer. Such DNAs encoding proteins functionally equivalent to an Ehd1 protein, obtainable by hybridization techniques or PCR techniques, are also included in the DNAs encoding Ehd1 proteins of this invention.

Hybridization reactions to isolate such DNAs are preferably conducted under stringent conditions. Stringent hybridization conditions of the present invention include conditions such as 6 M urea, 0.4% SDS, and 0.5×SSC, and those conditions yielding similar stringencies to these. DNAs with higher homology are expected to be isolated when hybridization is performed under more stringent conditions, for example, 6 M urea, 0.4% SDS, and 0.1×SSC. Herein, high homology means identity over the entire amino acid sequence of at least 50% or above, more preferably 70% or above, much more preferably 90% or above, and most preferably 95% or above.

The degree of homology of one amino acid sequence or nucleotide sequence to another can be determined using the BLAST algorithm by Karlin and Altschul (Proc. Natl. Acad. Sci. USA 87: 2264-2268, 1990; Proc. Natl. Acad. Sci. USA 90: 6873-5877, 1993). Programs such as BLASTN and BLASTX, developed based on the BLAST algorithm (Altschul et al. (1990) J. Mol. Biol. 215: 403-410), are also being used. To analyze a nucleotide sequence according to BLASTN, parameters are set, for example, at score=100 and word length=12. On the other hand, parameters used for the analysis of amino acid sequences by BLASTX are, for example, score=50 and word length=3. The default parameters for each program are used when using the BLAST and Gapped BLAST programs. Specific techniques for such analysis are known in the (see www.ncbi.nlm.nih.gov.)

DNAs of the present invention include genomic DNAs, cDNAs, and chemically synthesized DNAs. Genomic DNAs and cDNAs can be prepared according to conventional methods known to those skilled in the art. More specifically, genomic DNAs can be prepared, for example, by (1) extracting genomic DNAs from rice cultivars that comprise a DNA encoding an Ehd1 protein; (2) constructing a genomic library (utilizing a vector, such as a plasmid, phage, cosmid, BAC, PAC, and so on); (3) expanding the library; and (4) conducting colony hybridization or plaque hybridization using a probe prepared based on a DNA that encodes an Ehd1 protein of the present invention (e.g. SEQ ID NO.: 1, 2, 4, 5, 7, or 8). Alternatively, genomic DNAs can be prepared by PCR, using primers specific to a DNA encoding an Ehd1 protein of the present invention (e.g. SEQ ID NO.: 1, 2, 4, 5, 7, or 8). cDNAs can be prepared, for example, by (1) synthesizing cDNAs based on mRNAs extracted from rice cultivars that comprise a DNA encoding an Ehd1 protein; (2) preparing a cDNA library by inserting the synthesized cDNA into vectors, such as λZAP; (3) expanding the cDNA library; and (4) conducting colony hybridization or plaque hybridization as described above. Alternatively, cDNAs can be also prepared by PCR.

DNAs encoding an Ehd1 protein of the present invention can be used to promote plant flowering, for example. To prepare transgenic plants with promoted flowering, the above-described DNAs are inserted into appropriate vectors and introduced into plant cells using a method described below. Transgenic plants are regenerated from the transformed plant cells thus obtained. The present invention provides such methods for promoting plant flowering.

The present invention also provides methods for delaying plant flowering. Transgenic plants with delayed flowering can be obtained, for example, by inserting a DNA which suppresses the expression of an Ehd1 protein-encoding DNA into an appropriate vector; transforming the DNA construct into a plant cell using a method described below; and regenerating a plant from the resulting transformed plant cell. The step of suppressing the expression of Ehd1 protein-encoding DNAs includes suppressing the transcription of these DNAs, as well as their translation into proteins. In addition, it includes not only loss of DNA expression but also its reduction. It also includes the loss of an in vivo function of the translated proteins in plant cells.

Antisense techniques are the most commonly used methods in the art to suppress the expression of a specific endogenous gene in plants. Ecker et al. were the first to demonstrate the antisense effect of an antisense RNA introduced into plant cells by electroporation (J. R. Ecker and R.

W. Davis (1986) Proc. Natl. Acad. Sci. USA 83: 5372). After that, expression of antisense RNAs reportedly reduced target gene expression in tobacco and petunias (A. R. van der Krol et al. (1988) Nature 333: 866). Antisense techniques have now been established as a means for suppressing target gene expression in plants.

Multiple factors act in the suppression of target gene expression by antisense nucleic acids. These include: inhibition of transcription initiation by triple strand formation; inhibition of transcription by hybrid formation at a site where the RNA polymerase has formed a local open loop structure; transcription inhibition by hybrid formation with the RNA being synthesized; inhibition of splicing by hybrid formation at an intron-exon junction; inhibition of splicing by hybrid formation at a site of spliceosome formation; inhibition of mRNA translocation from the nucleus to the cytoplasm by hybrid formation with mRNA; inhibition of splicing by hybrid formation at a capping site or poly A addition site; inhibition of translation initiation by hybrid formation at a translation initiation factor binding site; inhibition of translation by hybrid formation at a ribosome binding site near the initiation codon; inhibition of peptide chain elongation by hybrid formation in a translated region or at an mRNA polysome binding site; and inhibition of gene expression by hybrid formation at a site of interaction between nucleic acids and proteins. These antisense nucleic acids suppress target gene expression by inhibiting various processes such as transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society), Tokyo Kagaku Dozin, pp. 319-347, (1993)).

The antisense sequences of the present invention can suppress target gene expression by any of the above mechanisms. In one embodiment, an antisense sequence designed to be complementary to an untranslated region near the 5' end of the mRNA of a gene is thought to effectively inhibit translation of that gene. Sequences complementary to coding regions or to an untranslated region on the 3' side can also be used. Thus, the antisense DNAs used in the present invention include both DNAs comprising antisense sequences against untranslated regions and against translated regions of the gene. The antisense DNAs to be used are conjugated downstream of an appropriate promoter, and are preferably conjugated to sequences containing the transcription termination signal on the 3' side. DNAs thus prepared can be transformed into a desired plant by known methods. The sequences of the antisense DNAs are preferably sequences complementary to an endogenous gene of the plant to be transformed, or a part thereof, but need not be perfectly complementary so long as they can effectively suppress the gene's expression. The transcribed RNAs are preferably at least 90%, and more preferably at least 95% complementary to the transcribed product of the target gene. In order to effectively suppress the expression of a target gene by means of an antisense sequence, antisense DNAs should be at least 15 nucleotides long, more preferably at least 100 nucleotides long, and still more preferably at least 500 nucleotides long. However, the antisense DNAs to be used are generally shorter than 5 kb, and preferably shorter than 2.5 kb.

DNAs encoding ribozymes can also be used to suppress the expression of endogenous genes. A ribozyme is an RNA molecule comprising catalytic activity. There are many ribozymes comprising various activities, and among them, research focusing on ribozymes as RNA-cleaving enzymes has enabled the design of ribozymes that cleave RNAs site-specifically. While some ribozymes of the group I intron type or the M1 RNA contained in RNaseP consist of 400 nucleotides or more, others belonging to the hammerhead-type or the hairpin-type comprise an activity domain of about 40 nucleotides (Makoto Koizumi and Eiko Ohtsuka (1990) Tanpakushitsu Kakusan Kohso (Nucleic acid, Protein, and Enzyme) 35: 2191).

The self-cleavage domain of a hammerhead-type ribozyme cleaves at the 3' side of C15 of the G13U14C15 sequence, and formation of a nucleotide pair between U14 and A9 at the ninth position is considered to be important for this ribozyme activity. It has been shown that cleavage may also occur when the 15th nucleotide is A15 or U15 instead of C15 (M. Koizumi et al. (1988) FEBS Lett. 228: 225). If a ribozyme is designed to comprise a substrate-binding site complementary to the RNA sequences adjacent to the target site, one can create a restriction-enzyme-like RNA-cleaving ribozyme which recognizes the UC, UU, or UA sequence within a target RNA (M. Koizumi et al. (1988) FEBS Lett. 239: 285; M. Koizumi et al. (1989) Nucleic Acids Res. 17: 7059). For example, in DNAs that encode Edh1 proteins (SEQ ID NO.: 2, 5, or 8), there are a number of sites that can be used as ribozyme targets.

Hairpin-type ribozymes are also useful in the present invention. These ribozymes can be found, for example, in the minus strand of satellite RNA in tobacco ringspot virus (J. M. Buzayan (1986) Nature 323: 349). Ribozymes that cleave RNAs target-specifically have also been shown to be produced from hairpin-type ribozymes (Y. Kikuchi and N. Sasaki (1992) Nucleic Acids Res. 19: 6751; Yo Kikuchi (1992) Kagaku To Seibutsu (Chemistry and Biology) 30: 112).

Transcription is enabled in plant cells by fusing a ribozyme, designed to cleave a target, with a promoter such as the cauliflower mosaic virus 35S promoter, and with a transcription termination sequence. If extra sequences have been added to the 5' end or the 3' end of the transcribed RNA, ribozyme activity can be lost. In such cases, one can place an additional trimming ribozyme, which functions in cis, on the 5' or the 3' side of the ribozyme portion, in order to precisely cut the ribozyme portion from the transcribed RNA containing the ribozyme (K. Taira et al. (1990) Protein Eng. 3: 733; A. M. Dzaianott and J. J. Bujarski (1989) Proc. Natl. Acad. Sci. USA 86: 4823; C. A. Grosshands and R. T. Cech (1991) Nucleic Acids Res. 19: 3875; K. Taira et al. (1991) Nucleic Acid Res. 19: 5125). Even greater effects can be achieved by arranging these structural units in tandem, enabling multiple sites within a target gene to be cleaved (N. Yuyama et al., Biochem. Biophys. Res. Commun. 186: 1271 (1992)). Thus, using these ribozymes, the transcription products of a target gene of the present invention can be specifically cleaved, thereby suppressing expression of the gene.

Endogenous gene expression can also be suppressed by RNA interference (RNAi), using double-stranded RNAs that comprise a sequence identical or similar to a target gene. RNAi refers to the phenomenon in which a double-stranded RNA comprising a sequence identical or similar to a target gene sequence is introduced into cells, thereby suppressing expression of both the exogenous gene introduced and the target endogenous gene. The details of the RNAi mechanism are unclear, but it is thought that an introduced double-stranded RNA is first degraded into small pieces, which somehow serve as a target gene indicator, resulting in degradation of the target gene. RNAi is known to be effective in plants as well (Chuang C F, Meyerowitz E M, Proc Natl Acad Sci USA 97: 4985, 2000). For example, in order to use RNAi to suppress the expression of DNAs that encode the Ehd1 protein in plants, Ehd1 protein-encoding DNAs (SEQ ID: 2, 5, or 8), or double-stranded RNAs comprising a sequence similar to these DNAs, can be introduced into the plants in question. Plants whose flowering is delayed compared to a wild-type plant can then be selected from the resulting plants. Genes used for RNAi need not be completely identical to a target gene; however, they should comprise sequence identity of at least 70% or above, preferably 80% or above, more preferably 90% or above, and most preferably 95% or above. Sequence identity can be determined by an above-described method.

Suppression of endogenous gene expression can be achieved by co-suppression, through transformation with a DNA comprising a sequence identical or similar to a target gene sequence. "Co-suppression" refers to the phenomenon wherein transformation is used to introduce plants with a gene comprising a sequence identical or similar to a target endogenous gene sequence, thereby suppressing expression of both the exogenous gene introduced and the target endogenous gene. Although the details of the co-suppression mechanism are unclear, at least a part is thought to overlap with the RNAi mechanism. Co-suppression is also observed in plants (Smyth DR, Curr. Biol. 7: R793, 1997; Martienssen R Curr. Biol. 6: 810, 1996). For example, if one wishes to obtain a plant in which a DNA encoding an Ehd1 protein is co-suppressed, the plant in question can be transformed with a vector DNA designed to express the DNA encoding the Ehd1 protein, or a DNA comprising a similar sequence. Plants whose flowering is delayed compared to a wild-type plant are then selected from the resultant plants. Genes for use in co-suppression do not need to be completely identical to a target gene, but should comprise sequence identity of at least 70% or above, preferably 80% or above, more preferably 90% or above, and most preferably 95% or above. Sequence identity may be determined by an above-described method.

The present invention provides methods for producing transgenic plants, wherein said methods comprise the steps of introducing a DNA of the present invention into plant cells, and regenerating plants from these cells.

In the present invention, cells can be derived from any plant, without limitation. Vectors used for the transformation of plant cells are not limited as long as they can express the inserted gene in the plant cells. Vectors that can be used include, for example, vectors comprising promoters (e.g., cauliflower mosaic virus 35S promoter) for constitutive gene expression in plant cells, and vectors comprising promoters that are inducibly activated by external stimuli. The term "plant cell" as used herein includes various forms of plant cells, such as culture cell suspensions, protoplasts, leaf sections, and calluses.

A vector can be introduced into plant cells by known methods, such as by using polyethylene glycol, electroporation, *Agrobacterium*-mediated transfer, and particle bombardment. *Agrobacterium* (for example, EHA101) mediated transfer can be carried out by, for example, the ultraspeed transformation of monocotyledon (Japanese Patent No. 3141084). Particle bombardment can be carried out by, for example, using equipment available from Bio-Rad. Plants can be regenerated from transformed plant cells by known methods and according to the type of the plant cell (see Toki et al., (1995) Plant Physiol. 100:1503-1507).

For example, methods for producing a transformed rice plant include: (1) introducing genes into protoplasts using polyethylene glycol, then regenerating the plant (suitable for indica rice cultivars) (Datta, S. K. (1995) in "Gene Transfer To Plants", Potrykus I and Spangenberg Eds., pp 66-74); (2) introducing genes into protoplasts using electric pulses, then regenerating the plant (suitable for *japonica* rice cultivars) (Toki et al. (1992) Plant Physiol. 100: 1503-1507); (3) introducing genes directly into cells by particle bombardment, then regenerating the plant (Christou et al. (1991) Bio/Technology, 9: 957-962); (4) introducing genes using *Agrobacterium*, then regenerating the plant (Hiei et al. (1994) Plant J. 6: 271-282); and so on. These methods are already established in the art and are widely used in the technical field of the present invention. Such methods can be suitably used in the present invention.

Once a transgenic plant is obtained, in which a DNA of the present invention has been introduced into its genome, progenies can be derived from that plant by sexual or vegetative propagation. Alternatively, plants can be mass-produced from breeding materials obtained from the plant (for example, from seeds, fruits, ears, tubers, tubercles, tubs, calluses, protoplasts, etc.), as well as from progenies or clones thereof.

A: a linkage map prepared using a segregating population of 2500 individual plants and RFLP markers. The labels above the line represent RFLP markers, and the numerals under the line indicate the number of recombinations detected in the intervals between respective markers;

B: a detailed linkage map using CAPS markers and prepared based on nucleotide sequence information; and C: a putative gene in the candidate genomic region, and genomic DNA fragments used in the transformation.

Figure 4:
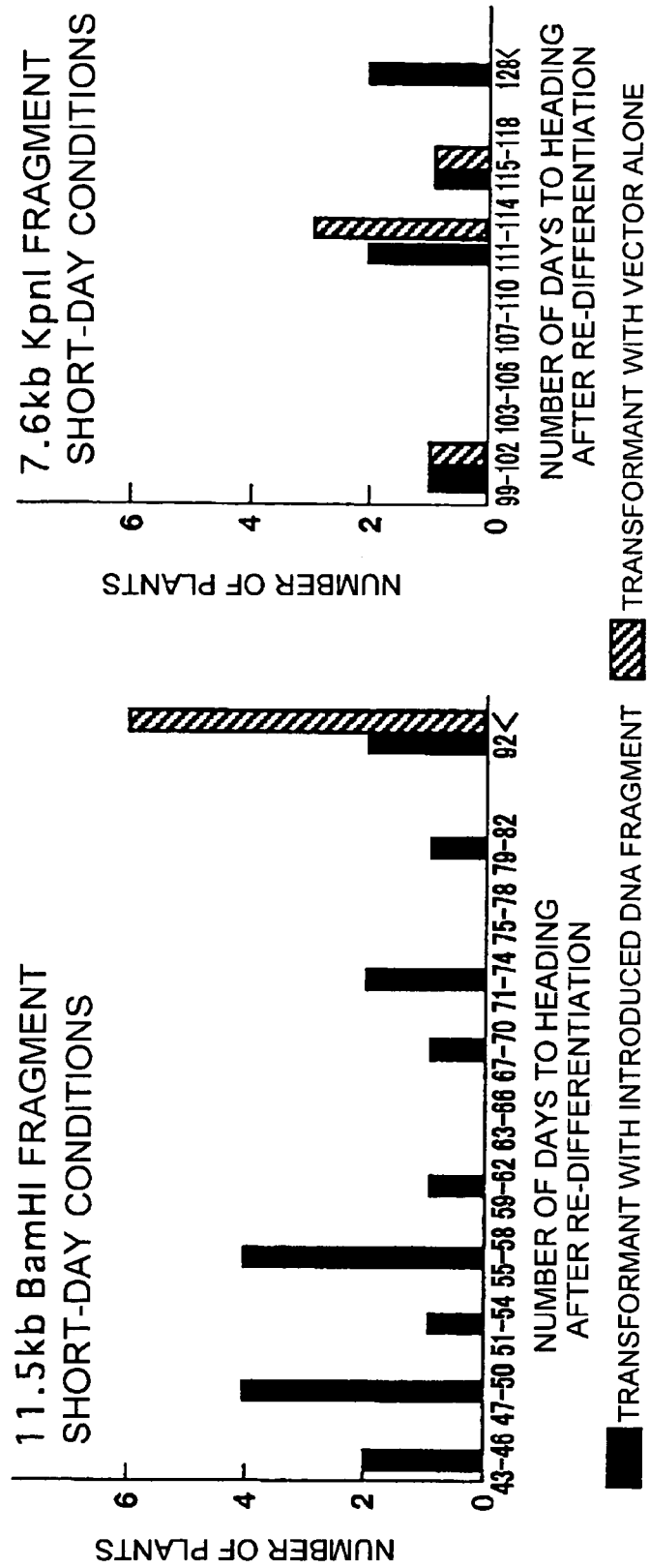

FIG. 4 depicts bar graphs showing the frequency distribution of the number of days to heading of a transformed plant (T0) produced by introducing either the 11.5 kb BamHI fragment or 7.6 kb KpnI fragment of Kasalath into Taichung 65, and cultivating under short-day conditions (ten hours of daylight).

Figure 5:
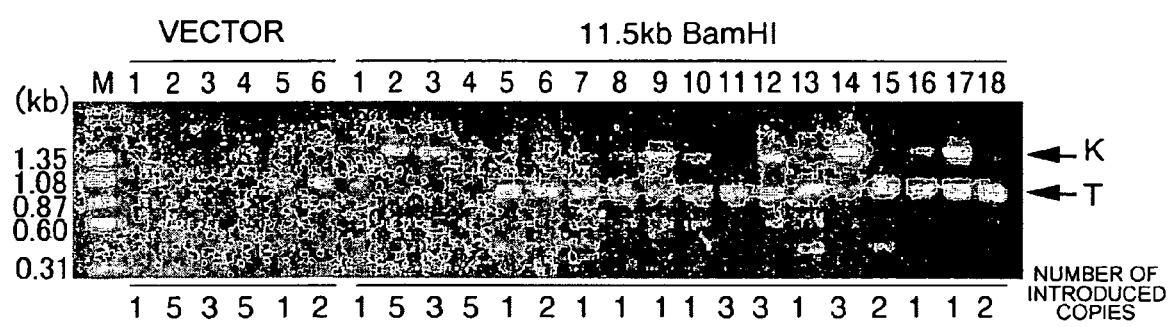

FIG. 5 is a photograph showing the presence or absence of Kasalath ARR-like gene expression in the individual transformed plants. Total RNA was extracted from each plant, reverse transcribed, PCR-amplified, and digested with DdeI. The sizes of products corresponding to the Kasalath and Taichung 65-derived mRNAs are shown with "K" and "T" respectively.

Figure 6:
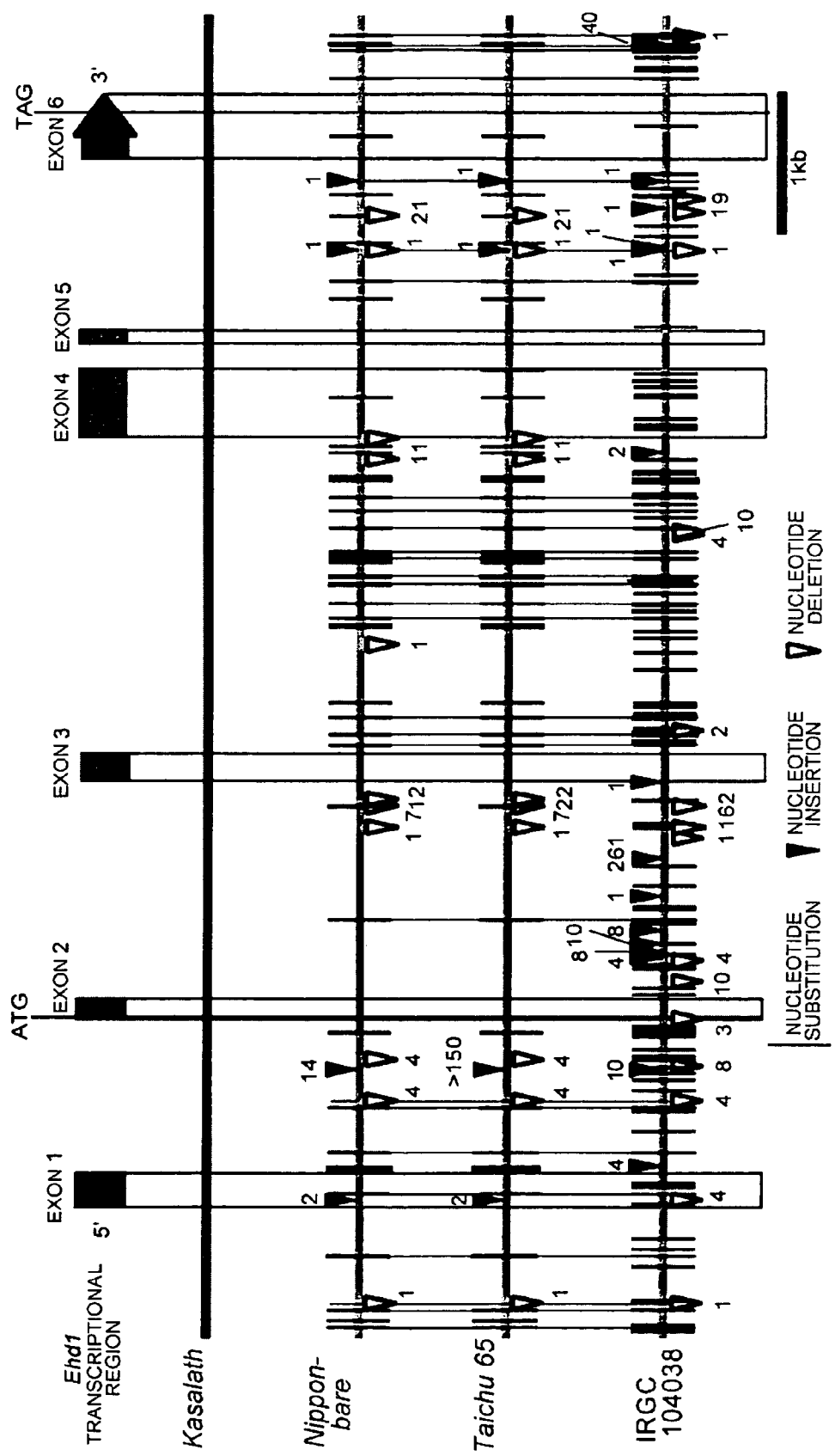

FIG. 6 is a diagram showing the Ehd1 gene structure and nucleotide sequence polymorphism.

FIG. 7 shows a comparison of Ehd1 protein amino acid sequences. The arrow indicates the position of the mutated amino acid found only in Taichung 65. The amino acid sequences of Taichung 65, Nipponbare, Kasalath, and IRGC 104038 are set forth in SEQ ID NOs. 12, 9, 6, and 3, respectively.

Figure 8:
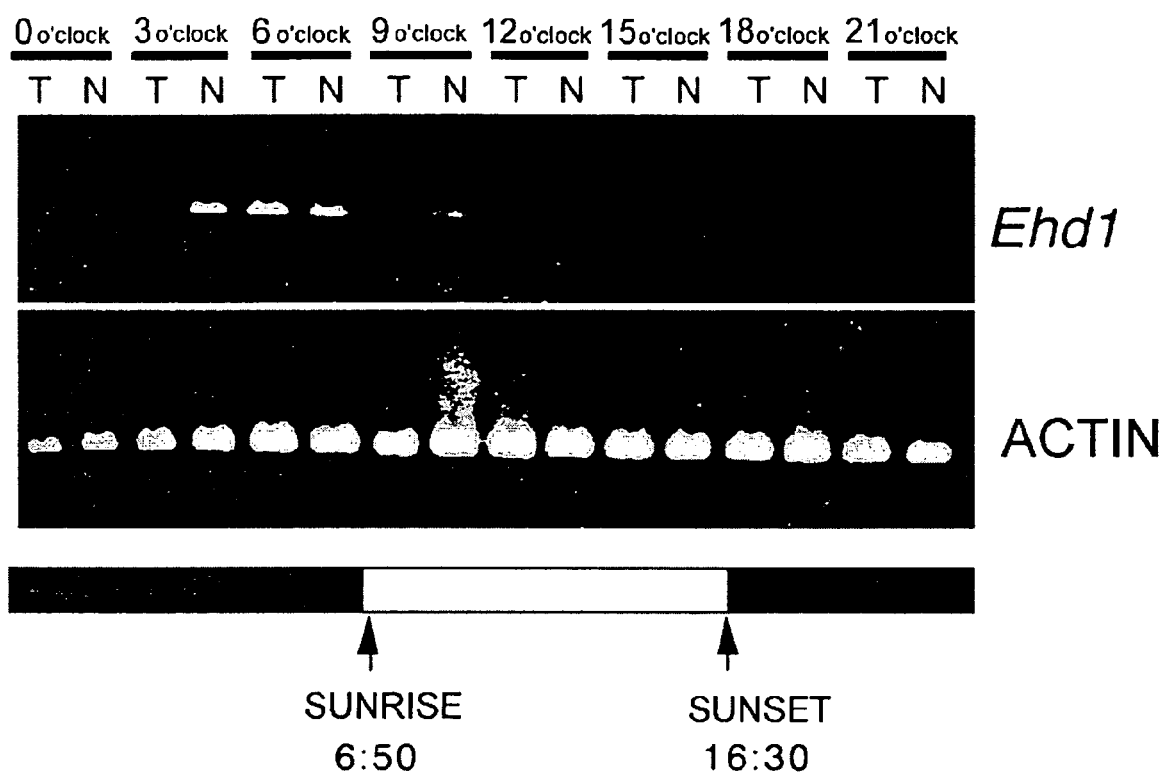

FIG. 8 represents a photograph and diagram showing changes in the amount of Ehd1 mRNA accumulated over a day. Four weeks after sowing, total RNA was extracted from the leaves of Taichung 65 (T) and nearly isogenic line T65(Ehd1) (N) of the Ehd1 gene of *O. glaberrima* Steud. (IRGC 104038), and RT-PCR analysis was performed over 30 PCR cycles.

BEST MODE FOR CARRYING OUT THE INVENTION

Herein below, the present invention is more specifically described with reference to Examples; however, it is not to be construed as being limited thereto.

EXAMPLE 1

The Heading-promoting Action of the Ehd1 Gene Under Short-day Conditions

Figure 1:
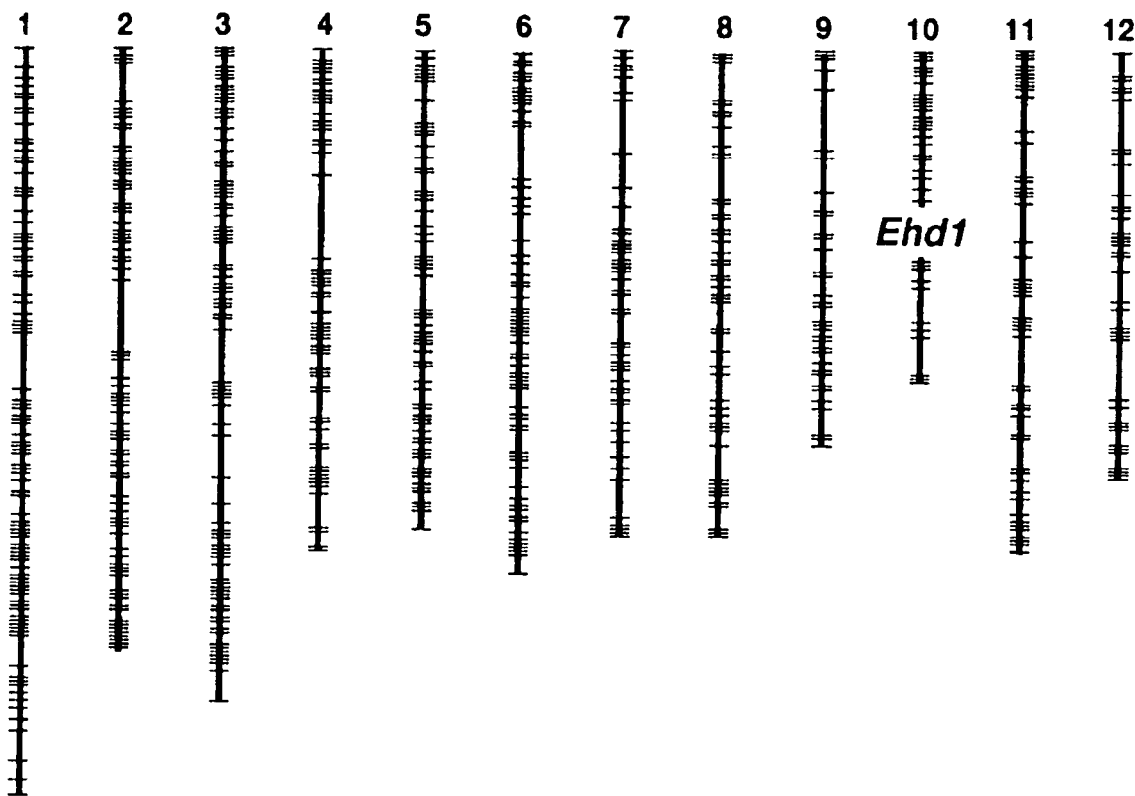
FIG. 1 is a diagram showing the Ehd1 locus on chromosomes.
Figure 2:
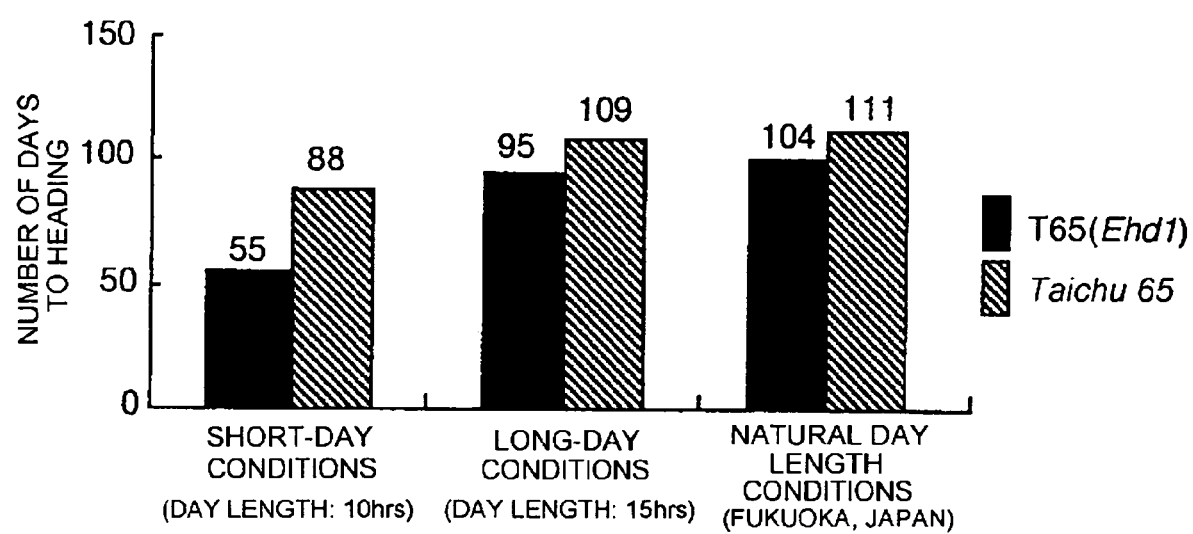
FIG. 2 is a bar graph showing the number of days until heading of nearly isogenic rice line T65(Ehd1) of the *O. glaberrima* Ehd1 gene, and its recurrent parent line (Taichung 65) under short-day, long-day, and natural day-length conditions. Under short-day and long-day conditions, plants were cultivated without transplantation in a day-light Kyushu University glasshouse. The results for natural day-length conditions are those of early season cultivation at Kyushu University (Fukuoka City) (sowed on May 2 and transplanted on June 14).

The Ehd1 locus is a QTL associated with heading time and detected using the progeny of a cross between *japonica* rice cultivar "Taichung 65" and West African region rice cultivar *O. glaberrima* Steud. (IRGC 104038). The Ehd1 locus has been proved to be located on the long arm of chromosome 10 (Doi et al., Breeding Science 49: 395-399, 1999) (FIG. 1). The Ehd1 gene of *O. glaberrima* (IRGC 104038) has been shown to comprise a heading-promoting action, and acts dominantly over the allele of Taichung 65. In this Example, both a nearly isogenic rice line T65(Ehd1), in which the Ehd1 region of Taichung 65 had been substituted with the Ehd1 gene of *O. glaberrima*, and Taichung 65 were cultivated under different day-length conditions to investigate the number of days until their heading. T65 (Ehd1) headed seven days earlier than Taichung 65 under natural day-length conditions, 14 days earlier under long-day conditions, and 33 days earlier under short-day conditions (FIG. 2). These results demonstrated that the Ehd1 gene comprised the function of promoting heading, and that its heading-promoting action becomes more prominent under short-day conditions.

EXAMPLE 2

High-resolution Linkage Analysis

Figure 3:
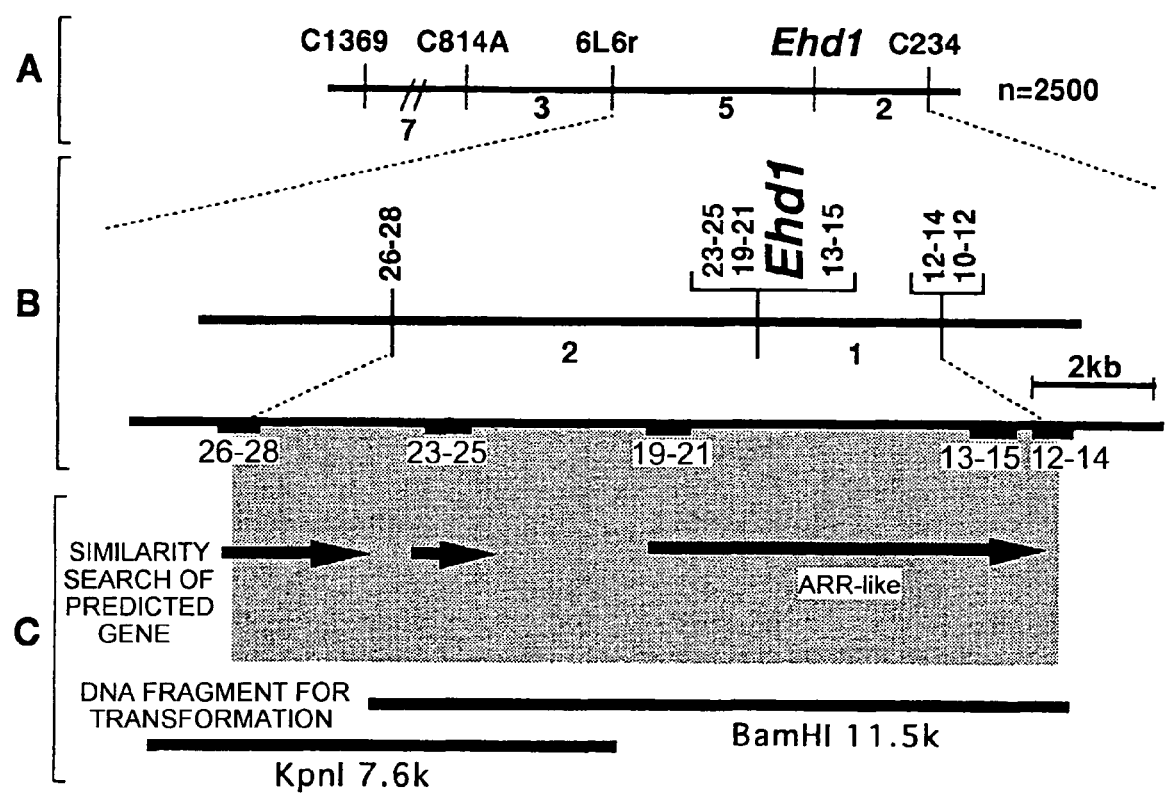
FIG. 3 represents a diagram showing a high-resolution linkage map and physical map of the Ehd1 region.

Genetic analysis performed hitherto has proven that the Ehd1 locus is positioned as a single gene locus (old name: Ef(t)) between RFLP markers C234 and G37, and co-segregated with C1369 (Doi, Taguchi, and Yoshimura: Japanese Society of Breeding, 94th lecture, Japanese Journal of Breeding (Suppl.), p 104, 1998). However, at the resolution level of this linkage analysis, it was difficult to isolate and identify genes using map-based cloning. In this example, detailed linkage analysis of the Ehd1 region was performed with a large segregating population essential for map-based cloning. A generation of progenies derived from backcrossing Taichung 65 and IRGC 104038 was used as the segregating population for linkage analysis. From these back-crossed progeny, plants were selected whose Ehd1 region was heterologous, and whose other genomic regions were mostly substituted with Taichung 65 type genome. These selected plants underwent self-fertilization, producing 2500 progeny plants (the F2 population). Those plants that comprise a chromosome with a recombination near the Ehd1 locus were selected using Ehd1-flanking CAPS (Cleaved Amplified Polymorphic Sequence) markers C1286 (primers [SEQ ID NO: 13/5'-CCAATGAAGGGTAAGTATCG-3'] and [SEQ ID NO: 14/5'-TGTGCTTAAGATACACGG-TAGTTCA-3'], restriction enzyme NruI); and G37 (primers [SEQ ID NO: 15/5'-CTGCAGCTTCCACCATGGCA-3'] and [SEQ ID NO: 16/5'-CAAGGGTGCATTCATTGCAC-CTCCTCTAGCCATGGCCTAATGATGCA-3'], restriction enzyme EcoT22I) The genotype of the Ehd1 locus was determined by a progeny test of the F3 generation. That is, 48 inbred progeny plants from the selected plants (F2) were cultivated in an experimental farm at Kyushu University to determine their Ehd1 genotype based on variations in the number of days until the heading of each line. The linkage analysis results located the Ehd1 locus between RFLP markers C814A and C234, identifying eight and two recombinant individuals between Ehd1 and these markers respectively (FIG. 3).

EXAMPLE 3

Identification of a Candidate Gene

The nucleotide sequences of the RFLP markers flanking the Ehd1 gene were found to be comprised in published genomic nucleotide sequences, such that the nucleotide sequence of Ehd1 candidate genomic region was obtained from published nucleotide sequence data (GenBank Accession No. AC027038). Using information on the nucleotide sequences of this candidate genomic region, novel CAPS markers were prepared for narrowing down the candidate genomic region. Ehd1 was found to have two recombinations with CAPS marker 26-28 (primers [SEQ ID NO: 17/5'-ACGCTGCAACAAAGAGCAGA-3'] and [SEQ ID NO: 18/5'-TTGTTGACGAAAGCCCATTG-3'], restriction enzyme MspI); and one recombination with 12-14 (primers [SEQ ID NO: 19/5'-GGAGATCATGCTCACGGATG-3'] and [SEQ ID NO: 20/5'-CAAGCAAACACGGAGCGACT-3'], restriction enzyme BamHI). Furthermore, the Ehd1 gene was co-segregated with CAPS markers 13-15 (primers [SEQ ID NO: 21/5'-CCTTGCATCCGTCTTGATTG-3'] and [SEQ ID NO: 22/5'-GGGCAAATTCCCTCCAGAGT-3'], restriction enzyme MspI); 19-21 (primers [SEQ ID NO: 23/5'-TTTGGATACGTACCCCTGCAT-3'] and [SEQ ID NO: 24/5'-GCGCAATCGCATACACAATAA-3' ], restriction enzyme MspI); and 23-25 (primers [SEQ ID NO: 25/5'-GAGCCCGAGCCCATGTATAG-3'] and [SEQ ID NO: 26/5'-TGGCTAAGATGGAGGGACGA-3'], restriction enzyme MboI). Therefore, the Ehd1 candidate region was narrowed down to a region of about 16 kb, flanked by CAPS markers 26-28 and 12-14. Gene predictions and similarity searches carried out against the nucleotide sequence of this candidate region using GENSCAN (http://genes.mit.edu/GENSCAN.html) proved the presence of three types of predicted genes. One type showed similarity to the two-component response regulator (ARR) gene of *Arabidopsis*. The other two types showed high similarity to rice EST, but no resemblance to known genes whose functions had been established. However, since none of these predicted genes could be excluded as Ehd1 candidates, transformation of these three types of predicted genes was used to verify function as Ehd1 candidates.

EXAMPLE 4

Functional Verification of Ehd1 Candidate Gene

A genomic DNA fragment derived from the indica rice cultivar Kasalath, which is assumed to comprise a functional Ehd1 allele, was used for the transformation. That is, a BAC library constructed from the genomic DNA of Kasalath (Baba et al., Bulletin of the NIAR 14: 41-49, 2000) was screened using a pair of primers 10-12 (SEQ ID NO: 27/5'-ATTGGGCCAAACTGCAAGAT-3' and SEQ ID NO: 28/5'-ACGAGCCTAATGGGGGAGAT-3') capable of amplifying the nucleotide sequence near Ehd1 to select BAC clone KBM128G10, which comprises the Ehd1 candidate gene. An 11.5 kb BamHI fragment comprising the ARR-like candidate gene and one of the predicted genes showing high similarity to the rice EST, and a 7.6 kb KpnI fragment comprising the two predicted genes other than the ARR-like candidate genes (FIG. 3), were excised from the BAC clone KBM128G10. These fragments were each incorporated into the Ti-plasmid vector pPZP2H-lac (Fuse et al., Plant Biotechnology 18: 219-222, 2001), and these transformed vectors were then introduced into Taichung 65, mediated by *Agrobacterium*. Regenerated plants were immediately transferred to growth chambers under short-day conditions (ten hours of daylight) and cultivated to investigate the number of days until heading. Almost all of the transgenic plants (T0) (18 plants) introduced with the 11.5 kb BamHI fragment headed earlier than the plants introduced with the vector alone (six plants) (FIG. 4). On the other hand, the number of days to heading in the six plants introduced with the 7.6 kb KpnI fragment was about the same as for the five plants introduced with the vector alone (FIG. 4). The expression of the Kasalath-derived ARR-like candidate gene in plants introduced with the 11.5 kb BamHI fragment was also confirmed by RT-PCR using a gene-specific marker (primers [SEQ ID NO: 29/5'-GAGATCAACGGCCACCGAAG-3'] and [SEQ ID NO: 30/5'-GTCGAGAGCGGTGGATGACA-3'], restriction enzyme DdeI). Transcription of the Kasalath-derived ARR-like candidate gene was observed in almost all of the plants (FIG. 5). Thus, the Ehd1 candidate could be narrowed down to the ARR-like candidate gene contained in the 11.5 kb BamHI fragment. Furthermore, to confirm that heading promotion was due to the transgene, individual plants comprising low copy numbers of the gene were selected from those transformed plants (T0) with earlier heading. Their self-fertilized progenies were cultivated under short-day conditions to investigate the number of days until heading. Each of the three types of progeny populations were divided into early-maturing plants (41-70 days to heading) and late-maturing plants (81 days or more to heading). All of the early-maturing plants retained the introduced Kasalath-derived ARR-like candidate gene, and headed at about the same time as the nearly isogenic rice line T65(Ehd1). On the other hand, the number of days to heading of Taichung 65 was 81 days or more, about the same as for late-maturing plants (Table 1). From the above-described results, the ARR-like candidate gene was shown to comprise heading-promotion function under short-day conditions, and to be the Ehd1 gene.

EXAMPLE 5

Nucleotide Sequence Analysis of the Ehd1 Candidate Gene

The genomic nucleotide sequences of approximately 7.6 kb Ehd1 regions were analyzed in rice cultivars *O. glaberrima* (IRGC 104038), Kasalath, Nipponbare, and Taichung 65 (TA repeats of 200 bp or more exist in Taichung 65; the exact number of these has not been determined). Compared to Kasalath, 60 or more nucleotide substitutions, insertions, and deletions were detected in this region in Nipponbare and Taichung 65, and at 140 positions or more in IRGC 104038 (FIG. 6). The full-length cDNA of IRGC 104038 was also determined, and as a result of comparing the genomic nucleotide sequences, Ehd1 was predicted to comprise six exons, with a full-length transcriptional region of 1316 bp and encoding a protein comprising 341 amino acids (FIG. 7). Comparison of differences in nucleotide sequences within the predicted transcriptional region with that of Kasalath detected four single-nucleotide substitutions and two-nucleotide insertions in Nipponbare; five single-nucleotide substitutions and two-nucleotide insertions in Taichung 65; and fourteen single-nucleotide substitutions and four- and three-nucleotide deletions in IRGC 104038. On comparing the amino acid sequences of the predicted translational products of IRGC 104038, Kasalath, and Nipponbare, and Taichung 65, it was revealed that seven amino acids are substituted between IRGC 104038 and Taichung 65, two amino acids between Kasalath and Taichung 65, and one amino acid between Nipponbare and Taichung 65 (FIG. 7). Of these, the substitution of glycine at the $219^{th}$ amino acid (G in IRGC 104038, Kasalath, and Nipponbare) to arginine (R in Taichung 65) was the only mutation occurring in Taichung 65 alone (FIG. 7). This glycine had been highly conserved among the known ARR gene families. These facts suggested that this amino acid mutation is associated with the reduced function of Ehd1 derived from Taichung 65.

The genomic nucleotide sequences of the Ehd1 regions of *O. glaberrima* (IRGC 104038), Kasalath, Nipponbare, and Taichung 65 are set forth in SEQ ID NOs: 1, 4, 7, and 10 respectively; the nucleotide sequences of cDNAs thereof are set out in SEQ ID NOs: 2, 5, 8, and 11 respectively; and the amino acid sequences of the proteins encoded by these DNAs are set out in SEQ ID NOs: 3, 6, 9, and 12, respectively.

TABLE 1

| Progeny population | Number of days to heading (days) | | | | | | | | |
|---|---|---|---|---|---|---|---|---|---|
| | 41-45 | 46-50 | 51-55 | 56-60 | 61-65 | 66-70 | 71-75 | 76-80 | >81 | Total |
| Population 1 | 4 | 21 | 2 | — | — | — | — | — | 5* | 32 |
| Population 2 | — | 1 | 7 | — | 7 | 4 | — | — | 8* | 27 |
| Population 3 | — | 2 | 17 | — | 1 | — | — | — | 5* | 25 |
| Taichung 65 | — | — | — | — | — | — | — | — | 5 | 5 |
| T65(Ehd1) | — | 1 | 2 | — | — | — | — | — | — | 3 |

*The introduced gene was not retained.

EXAMPLE 6

Expression Analysis of the Ehd1 Candidate Gene

Variations of the Ehd1 gene expression level over a one-day period were examined for T65(Ehd1) in which the Ehd1 region of Taichung 65 had been substituted with a chromosomal fragment derived from IRGC 104038. T65 (Ehd1) and Taichung 65 were sowed in experimental greenhouses (at Tsukuba City, Ibaraki Prefecture) during the last ten days of December (sunrise: 6:50 AM, sunset: 4:30 PM; short-day conditions), cultivated for four weeks, and then the leaves were collected from both rice lines every three hours over 24 hours for analysis. Total RNA was extracted from these materials, and RT-PCR was performed for the Ehd1 gene using a pair of primers (sense strand [SEQ ID NO: 31/5'-TGGATCACCGAGAGCTGTGG-3'] and an antisense strand [SEQ ID NO: 32/5'-ATTTCCTTGCATC-CGTCTTG-3']). As a result, the transcriptional product of this gene was found to accumulate in large amounts around dawn (3 and 6 o'clock), with a tendency to decrease to undetectable levels after sunset till midnight (18 and 21 o'clock) (FIG. 8). Such circadian fluctuation in gene expression level is a phenomenon often observed in genes associated with photoperiod sensitivity, indicating some sort of association of this Ehd1 gene with photosignal transduction. From the above-described results, the candidate gene identified by map-based cloning was judged to be the Ehd1 gene promoting rice heading.

INDUSTRIAL APPLICABILITY

In conventional rice breeding, flowering (heading) time has been altered by (1) selection of early-maturing and late-maturing varieties by crossing, (2) mutagenesis by radiation and chemicals, and so on. However, these procedures posed problems such as the requirement of long periods of time for successful breeding, and the inability to control the degree or direction of variation. The present invention has enabled the establishment of a novel method for modifying plant flowering time by utilizing the isolated Ehd1 gene. Therefore, by transforming a sense strand of Ehd1 gene into a plant cultivar in which the function of this gene has been lost, for example, into Taichung 65 rice, rice heading (flowering) can be promoted under short-day conditions. At the same time, by introducing the Ehd1 gene in the antisense direction into a plant cultivar in which the function of the Ehd1 gene is retained, for example, into Nipponbare or Kasalath rice, expression of the endogenous Ehd1 gene can be suppressed to delay heading (flowering). Since this alteration can be expected to occur not only under short-day conditions but also under long-day or natural day-length conditions, the present invention is effective in controlling heading time (flowering time) under various cultivation conditions. Since the period of time required for transformation is extremely short compared to that required for gene transfer by crossing, flowering time can be modified without altering other characteristics. The use of the isolated Ehd1 gene to promote flowering is expected to be useful in simple alteration of the flowering time of plants such as rice, and to contribute to the breeding of plants adapted to different locations.

SEQUENCE LISTING

```
<160> NUMBER OF SEQ ID NOS: 32

<210> SEQ ID NO 1
<211> LENGTH: 7803
<212> TYPE: DNA
<213> ORGANISM: Oryza sativa
<220> FEATURE:
<223> OTHER INFORMATION: genomic DNA
<220> FEATURE:
<221> NAME/KEY: exon
<222> LOCATION: (743)..(931)
<220> FEATURE:
<221> NAME/KEY: intron
<222> LOCATION: (932)..(1830)
<220> FEATURE:
<221> NAME/KEY: exon
<222> LOCATION: (1831)..(1945)
<220> FEATURE:
<221> NAME/KEY: intron
<222> LOCATION: (1946)..(3440)
<220> FEATURE:
<221> NAME/KEY: exon
<222> LOCATION: (3441)..(3593)
<220> FEATURE:
<221> NAME/KEY: intron
<222> LOCATION: (3594)..(5422)
<220> FEATURE:
<221> NAME/KEY: exon
<222> LOCATION: (5423)..(5824)
<220> FEATURE:
<221> NAME/KEY: intron
<222> LOCATION: (5825)..(5973)
<220> FEATURE:
<221> NAME/KEY: exon
<222> LOCATION: (5974)..(6050)
```

```
<220> FEATURE:
<221> NAME/KEY: intron
<222> LOCATION: (6051)..(7034)
<220> FEATURE:
<221> NAME/KEY: exon
<222> LOCATION: (7035)..(7414)
<220> FEATURE:
<221> NAME/KEY: CDS
<222> LOCATION: (1837)..(1945)
<220> FEATURE:
<221> NAME/KEY: CDS
<222> LOCATION: (3441)..(3593)
<220> FEATURE:
<221> NAME/KEY: CDS
<222> LOCATION: (5423)..(5824)
<220> FEATURE:
<221> NAME/KEY: CDS
<222> LOCATION: (5974)..(6050)
<220> FEATURE:
<221> NAME/KEY: CDS
<222> LOCATION: (7035)..(7319)

<400> SEQUENCE: 1
ggtacctatt tgtttcatat ttttgctcga cattatctga gtttgtatcc atattcagca      60
ctatccgtgt ttgatccgat tccgattata aaatatgggt taggatatgg gaagggtaag     120
atccgaccga acccgacccg ttttcacccc tacacgtcgc taatctacac ttcgaggcaa     180
aaaaaaaaga gagcaacaaa tcaaactaca aaagcgcgca atcgcataca caataattaa     240
atttgtatct atcgtcacat atacaaataa aatttgatct tgcatatttg caccacaata     300
aggtaatacc tatgttttct acttttttaga aaatttatta ataacttttt ttagataatt     360
tatgaataac tatttggacc acaggaaata acaacgtag tacgacacat tctttcctag     420
gtcttatgta cgcatgattg tgtgtatatt ctcgccgacg ccgacgacgg tgaccggtgc     480
atatgttccc agccgtcctc cgccgcgcgt tgcggttgtg gaggaaggga gctccacgtc     540
tcgccatggc cgtccacaac ctcagttaga tctctagcta cctgatcccc aaaccctctc     600
aaaaagatgt atattcttcc tagcactctg gcccctggat tagctcaaaa attcctcata     660
tatatgctgg ctagctagct gatagtatat actactcata acccattctt cttccttacc     720
tagctagcta gcaaacactg aagctgggag ctctggctat atctccatat atatactaca     780
tcattgctat agctagctag ctggaggagg aacattcata cttaattcta gttacttgga     840
gtgagtttaa aacactgaat ttggtgaaat tgactggtgg ccgctgactg ctggcaggct     900
agctttggtg attaattaat tatctctcgg agtaagtctt ctatttgata tcacatgcat     960
ggaagaaggt atatatatat gtctacgcca acattcatgt acttagtcct ctactatttc    1020
tacatagtta attacaaccc accattaact gtattaatta cttagaactc tcacatttaa    1080
ccacgtcatg atcatatcaa cggtgttatc catcaattga ggtgtgtcgt ctatgagata    1140
tcagcaatta attaagatca acatttctca gcaaggagc tctaaaaccc tgctgcaaat     1200
atgcaggggt acgtatccaa atatatcata taccctgtc gtatatagta tttacatgta     1260
gttattgatg atgatagatt gctcatgcat ggaggttatt atttcttgtg tgtttggttt    1320
gttttgcctg gaaatagcta tagctttgca catatagctg cttaaatatt cttgaatgca    1380
gacatacgag ttttcgatat atactcagat atattagtac agtattatta tttgtatgca    1440
tatcatcagt gactcgattg atatttgaag atatatactt acataaaaat gcaaggatat    1500
atgcatgaag aacatgtcca tatgtgtata tatatatata tatctagaga tctctgtgtc    1560
tagcttgcac tacaccatat atatatatat aaaacctacc ttagccaaag gagtcagtta    1620
ctaactgtag ttagcattat tgttgaatta attctatacc tcattaacta tatatggtgc    1680
```

```
acgcgcattc catgcatcat gcatgtttat tactcgtcat atattatata tgatgtaaac    1740
acaaagtaca attgattata ttattattaa ttattttta aaaaacggag aagcagatat    1800
agtcgttaat ttttgttttc tcctaattag gttata atg gat cac cga gag ctg     1854
                                          Met Asp His Arg Glu Leu
                                           1               5 tgg cct tat gga cta aga gtt ctg gtc atc gat gac gac tgt tca tac     1902
Trp Pro Tyr Gly Leu Arg Val Leu Val Ile Asp Asp Asp Cys Ser Tyr
            10              15                  20 ttg tca gtc atg gaa gat tta ctt ctg aag tgc agc tac aag g           1945
Leu Ser Val Met Glu Asp Leu Leu Leu Lys Cys Ser Tyr Lys
        25              30              35 gtaaaatac catctataca aaacacataa ttaattaaca aatctaact atctagcttg     2004 gcacatatag tgatcgaata tattgatgcg aattaagatt atacatataa aatattgagt   2064
ttttctggat taaatagaag atgcatacag aagttacaaa cacgcaccac tacacacgtg   2124
cccatgcaca ctaatgtctc tcctaataca tgctcagata cgctcagata dacagatcag   2184
atcaattaat ggcaaatctt taacctcact aaaatcctat ggaagtata cttgtatgtg    2244 cataaaattt gtaaataaga tttaaaccct agtgtataag atcattaatt tttctactat   2304
ttaagttcag tcagtttcac atgcataata catgataatc ctatattatg tatatatata   2364
tatatatcat tccatgctta ctttaaccaa atttccctc caccttggtg tagccaatgc    2424
atcatataat tataatatgt tatgaataca taaatatata gcagaattta tgttcattgg   2484
cacataaaat gtgtttgcat gattcctatt attaaaataa atatttggta atgtgtttca   2544
gctaacaggc acatggaaat atagtcaaag atgatcagct ctgtggttgg actgccattt   2604
gctttgaaga agctacaaaa cttaattaa ttttgaaaat gaaataaaac atgcgggagt    2664
tctatatagt gtatatacct taaaataatt cttttctttc ttcccattta gtttgtcaaa   2724
ttagactgca agtagtaatt aaatcaaagt cttggagggt agtgcagaac atatattaag   2784
aacaaaggta ctccctccat actcataaag gaaggcgttt aggacatcga cacggtctct   2844
aaaacacaac tttgacttct tgtttctata aaaatattca ttgaaaaatg atatatgtat   2904
acttttatga agtaattt caagacaaat ctattcatat aatttttaca ttttcaaact    2964
caacaacttg agagttattc atgatttata ttcccaaggt ttgactctaa cattgtccta   3024
aacgatttca tttataagta cggagggagt atactttaat tatatatcct caccttgcag   3084
ttgcggtttc tagggttagc atatattttg tgaggtgtca actcagatat tgtgatgaca   3144
aattaaccta taaattttct ccatatgttt tattcaatgg gcgatccata ctccataaaa   3204
tgcatattaa ttaacttgta atgaaaaccg ggaaaagatg tgttcgtata taccaaga    3264 atcttgcaag aaagtgattg tatgtagtaa catttccata cacacatgaa gttacagata   3324
tatctatata gtctaacgtc aaaaatgaaa ttcttctaga tatatcttac aaatattcga   3384
tattggcctc attttctttg tgatgtatgt acctatatt agtatttctc ttgtag tt    3442
                                                              Val aca acg tat aag aac gtc aga gaa gct gtg cct ttc ata ttg gac aat     3490
Thr Thr Tyr Lys Asn Val Arg Glu Ala Val Pro Phe Ile Leu Asp Asn
        40              45                  50 cca caa ata gtt gac cta gta atc agt gat gcg ttc ttt cct acc gaa     3538
Pro Gln Ile Val Asp Leu Val Ile Ser Asp Ala Phe Phe Pro Thr Glu
        55              60              65 gat ggt ttg ctc att ctg caa gaa gta acc tcc aag ttt ggc ata cct     3586
Asp Gly Leu Leu Ile Leu Gln Glu Val Thr Ser Lys Phe Gly Ile Pro
70              75              80              85
```

-continued

```
aca gtg a gtaagtaat ttatttatta tctccttaca cattcttact agtttatatg      3642
Thr Val gattacacgc cttaacttac gcgtgcatgt gtgcttgagg aactaggtca aatatgcact    3702
gatatataat acgctactca ctgtctcaaa atataactac tttcgctacg tgcgggtcag    3762
gtcatctgtg atgggcccaa accgtacctc tgacaggttc ggccctcatt agagattagt    3822
tgtcagccta ctcacctctg acgggccgtt agaaatgggt gtcacaggt gactcacgtg     3882 tgacgtgtgg ctcttttccaa catgtcagag gtgactgtca cctttgacgg gttgtatttt   3942
atcacttatc acaggtgtga aaaacaacc caaaagaaaa agcaaaagcc ctcagcccca     4002
agctcacgcc aagagcataa cacaacatct ttgcatttta ttggcagatc tgataacatc    4062
caagaaaaaa ctacatatga aacaaagat gtatgataca tatcaaactt gagtaacaat     4122
atacatcaca caagtaatga tctccatcct aacaaactac acatccacac aagtaacaaa    4182
gaatatggcc caatttgaaa tttgcagtg aacatttgca agatatgaaa tcaagaacaa     4242
cctacaggag tgtcaagttc agggaggccg ccgtgctccc cctccacccc tgtcagatct    4302
acccaccaac tccaccacca gatctgccaa tcctccaggg tcagagaggc cagatccacg    4362
ctcgaggaga gcctagatcc gcacttgtga tagggacggc taccattgct ttggaccgga    4422
ggagacgagg aaatggcatc aatgatcggg gaggctagat ctgcacccga aaggcagct    4482 ggtgcttgag ggtagaggag acagcggcca acagtcggat cgatccaagt cccccgacct    4542
tgtggaggct agatcccatg gtcgccggat gctggcggag atgggggagc ccgggctcgg    4602
gggagaggct ggctccggtg gccggcggtt gggtgataaa ggaggaggcg gccaacagtc    4662
aagggagagg ccgcggcggc cggtgattgg gggaaggagg acgcaacggc tggtgatcgg    4722
ggaaaggagg aggcggtagc cgaatccacg tcctggaggc aagatccggc gaccggtgat    4782
caggaggcgg ttaggggaag agagtttgag atatgggat aaggatgaga gggagaaagt     4842
gagcagatgt gaggagaaga agagagaccg gaggatggga agggagttgg gccgtacaca    4902
tggggattgg gggattttcc tttattttaa attatcattg acgagcataa gaatttaata    4962
cgttagatat gaggtatcac atcctgtgat gaggtgcaaa ctcaacaccc gtcacagata    5022
gaaggtcata tatgcaggc ctatatgtgg gcccgtcaaa gatgttatgt gtcgagtcct     5082
cataaatgtc tgtgagatga gttttactt gtgacgagcc atcccttga accccatcta      5142 caactggcta tagttcaacc ccatcagaaa tgatgtcatt cgtgacgaga cattggcccg    5202
tcatagatag gccgtcacaa tgggatgctc tagtgaagtg ttcgagaatt caaattcgtc    5262
tcaaccaatc acaatcattt aatttattca cctatttttt ttatctcaac caatcgcaat    5322
catttttttt tataaatagc aatatttga gacaaaagga tcgagtaca ccctaataag      5382 ttcactcaca aggaaacttt atatatgttt ttttaactag tt atg gct tca agt       5436
                                              Ile Met Ala Ser Ser
                                                            90 gga gac aca aat aca gtg atg aaa tat gtt gca aat ggc gct tct gat     5484
Gly Asp Thr Asn Thr Val Met Lys Tyr Val Ala Asn Gly Ala Ser Asp
     95                  100                 105 ttc ctg cta aaa ccg gtg agg atc gaa gag ctg agc aac atc tgg cag     5532
Phe Leu Leu Lys Pro Val Arg Ile Glu Glu Leu Ser Asn Ile Trp Gln
    110                 115                 120 cac ata ttc cga aag caa atg caa gat cac aag aac aat aac atg gtt    5580
His Ile Phe Arg Lys Gln Met Gln Asp His Lys Asn Asn Asn Met Val
125                 130                 135                 140 gga aat ctc gaa aaa ccc ggt cat cct cca tca ata tta gcc atg gct    5628
```

-continued

```
Gly Asn Leu Glu Lys Pro Gly His Pro Pro Ser Ile Leu Ala Met Ala
            145                 150                 155 cgt gct act ccg gct acc acc aaa tca acg gcc acc gaa gct ttg cta    5676
Arg Ala Thr Pro Ala Thr Thr Lys Ser Thr Ala Thr Glu Ala Leu Leu
                160                 165                 170 gcg cct cta gaa aat gag gtg aga gat gac atg gtc aac tac aat ggt    5724
Ala Pro Leu Glu Asn Glu Val Arg Asp Asp Met Val Asn Tyr Asn Gly
        175                 180                 185 gag atc acg gac ata cga gac ctt aga aag tcc agg ctg acc tgg acc    5772
Glu Ile Thr Asp Ile Arg Asp Leu Arg Lys Ser Arg Leu Thr Trp Thr
    190                 195                 200 acg cag ttg cac cgt cag ttc att gcg gca gtg aac cac ctc gga gaa    5820
Thr Gln Leu His Arg Gln Phe Ile Ala Ala Val Asn His Leu Gly Glu
205                 210                 215                 220 gac a gtgagtgat caaattaaac ttctttgcag taccatttca atcactttc         5873
Asp atatgtatac atgcgtgtat acattaattt taatttacta gtatatatgt atttcctagc  5933
ttgttttaag atgtggtaat tatgtgtaat ttatttgcag ag gca gtt cca aag     5987
                                              Lys Ala Val Pro Lys
                                                              225 aag ata cta ggg ata atg aag gtc aaa cat ttg aca aga gag caa gtt    6035
Lys Ile Leu Gly Ile Met Lys Val Lys His Leu Thr Arg Glu Gln Val
            230                 235                 240 gcc agt cat ctg cag gtaatatttc agtggcttat tgcaagatga agcaaaacc     6090
Ala Ser His Leu Gln
            245 tatcatgttt ttcctttcaa gatttcttta cgataaatta gaccatatgc aagatatata  6150 caagggcaaa ttccctccag agttttttaga aaacactttc caatgtataa tatgtaaaaa 6210 tgtgttgtcc atgttacaat gattcttaat tatgctactt tcacaattgt acatataaat  6270 tagcctaata ctactcatac atatgtatca ggtacacatt gtaagtttat atatttgtat  6330 cactctaatg tactccctag ctctgtccat gaatacaatg gattataccc aattaagaag  6390 aaactaagaa agtgggtaaa gtacgcactg ctgctcatga tggagtatta ctagtagtac  6450 attctctcta ttttttttggg tagggatgat ggggagtagt gctagtagat ttttttttctc 6510 tttttttttat agaaccgatg gggtaaata aatggaagct gctggtatat gaattactga  6570 ctattgttct ctttgctttc ctaatactta tattcttgat aaactagagg cagggtttga  6630 aatttcgaaa ttggatttta tgccgggggt gaacgaaatt accgaaaatt tctggccgga  6690 attatttgaa aatttgactg aatttgaata aaatttgact aaattcacaa aaaattgcaa  6750 aaaaaactga aaattttagg cgagatttga gcatgccggt ggagggcaaa atttcggaaa  6810 attcgaatca aaatttcaaa ccctgactag aggatcataa tcatattgat ggacagaggg  6870 agcatgaatg aatatgaccg atgcttctag ggtttccttc tacaagcatc ctaattagct  6930 tattcaagtt agagtgcatc cactgcacaa cttctttcgc tgcttcttca gctaattcag  6990 ttgaacatat ataaccataa aacctaacat ttgaactgat gcag aaa tac agg atg   7046
                                                  Lys Tyr Arg Met
                                                              250 caa ctg aag aaa tcg att cca aca aca agc aaa cac gga gcg act ttg    7094
Gln Leu Lys Lys Ser Ile Pro Thr Thr Ser Lys His Gly Ala Thr Leu
            255                 260                 265 tca tcc acc gct ctc gac aaa aca caa gac cac cct tca aga tcg cag    7142
Ser Ser Thr Ala Leu Asp Lys Thr Gln Asp His Pro Ser Arg Ser Gln
        270                 275                 280 tat ttc aat caa gac gga tgc atg gaa atc atg gac tac tct tta ccg    7190
```

-continued

```
                        Tyr Phe Asn Gln Asp Gly Cys Met Glu Ile Met Asp Tyr Ser Leu Pro
                            285                 290                 295 aga gat gac ctc tca agt ggc tca gag tgc atg ctt gaa gaa cag aac         7238
Arg Asp Asp Leu Ser Ser Gly Ser Glu Cys Met Leu Glu Glu Gln Asn
300                 305                 310                 315 gat tac tca tcc gaa ggt ttc caa gat ttc cga tgg gat tca gac aaa         7286
Asp Tyr Ser Ser Glu Gly Phe Gln Asp Phe Arg Trp Asp Ser Asp Lys
                320                 325                 330 cag gaa tat gga cca tgt ttt tgg aat ttc tag gtagagaata taatgatccc       7339
Gln Glu Tyr Gly Pro Cys Phe Trp Asn Phe
            335                 340 atcatgtctc atgatccaca tccatatgtt gatacctgca attgactttc tgaataagtg       7399
aacattacca catccatata tactcttgat gttcattgca gaactaaact gacaacatac       7459
tgtacatagg ttgtctactc tatctagatg tgtcacatgc aaagattatg ttgataacat       7519
tcatccaaat caatgtccat cttctcaatt atgggtgtgt ttggggaagc tttagattct       7579
gagaagttgc tgaagataat acatgcatct aggtggcgac aatctagaga tgccgaggaa       7639
accaactttt ggcttatagt tcattttctg gattttacaa ttacaatttc ccaaaatcta       7699
gacgaaaagc tatactactg tttggtgagc ttttaattat gggatatatg gatatattcc       7759
tacatataag atccgtaatc ggaaaataaa caatatatgg atcc                        7803

<210> SEQ ID NO 2
<211> LENGTH: 1322
<212> TYPE: DNA
<213> ORGANISM: Oryza sativa
<220> FEATURE:
<223> OTHER INFORMATION: cDNA
<220> FEATURE:
<221> NAME/KEY: CDS
<222> LOCATION: (196)..(1221)

<400> SEQUENCE: 2
gctgggagct ctggctatat ctccatatat atactacatc attgctatag ctagctagct         60
ggaggaggaa cattcatact taattctagt tacttggagt gagtttaaaa cactgaattt        120
ggtgaaattg actggtggcc gctgactgct ggcaggctag ctttggtgat taattaatta        180
tctctcggag ttata atg gat cac cga gag ctg tgg cct tat gga cta aga         231
                Met Asp His Arg Glu Leu Trp Pro Tyr Gly Leu Arg
                1               5                   10 gtt ctg gtc atc gat gac gac tgt tca tac ttg tca gtc atg gaa gat         279
Val Leu Val Ile Asp Asp Asp Cys Ser Tyr Leu Ser Val Met Glu Asp
        15                  20                  25 tta ctt ctg aag tgc agc tac aag gtt aca acg tat aag aac gtc aga         327
Leu Leu Leu Lys Cys Ser Tyr Lys Val Thr Thr Tyr Lys Asn Val Arg
    30                  35                  40 gaa gct gtg cct ttc ata ttg gac aat cca caa ata gtt gac cta gta         375
Glu Ala Val Pro Phe Ile Leu Asp Asn Pro Gln Ile Val Asp Leu Val
45                  50                  55                  60 atc agt gat gcg ttc ttt cct acc gaa gat ggt ttg ctc att ctg caa         423
Ile Ser Asp Ala Phe Phe Pro Thr Glu Asp Gly Leu Leu Ile Leu Gln
                65                  70                  75 gaa gta acc tcc aag ttt ggc ata cct aca gtg att atg gct tca agt         471
Glu Val Thr Ser Lys Phe Gly Ile Pro Thr Val Ile Met Ala Ser Ser
            80                  85                  90 gga gac aca aat aca gtg atg aaa tat gtt gca aat ggc gct tct gat         519
Gly Asp Thr Asn Thr Val Met Lys Tyr Val Ala Asn Gly Ala Ser Asp
        95                  100                 105 ttc ctg cta aaa ccg gtg agg atc gaa gag ctg agc aac atc tgg cag         567
Phe Leu Leu Lys Pro Val Arg Ile Glu Glu Leu Ser Asn Ile Trp Gln
```

```
                                                                    -continued cac ata ttc cga aag caa atg caa gat cac aag aac aat aac atg gtt         615
His Ile Phe Arg Lys Gln Met Gln Asp His Lys Asn Asn Asn Met Val
125             130                 135                 140 gga aat ctc gaa aaa ccc ggt cat cct cca tca ata tta gcc atg gct         663
Gly Asn Leu Glu Lys Pro Gly His Pro Pro Ser Ile Leu Ala Met Ala
            145                 150                 155 cgt gct act ccg gct acc acc aaa tca acg gcc acc gaa gct ttg cta         711
Arg Ala Thr Pro Ala Thr Thr Lys Ser Thr Ala Thr Glu Ala Leu Leu
        160                 165                 170 gcg cct cta gaa aat gag gtg aga gat gac atg gtc aac tac aat ggt         759
Ala Pro Leu Glu Asn Glu Val Arg Asp Asp Met Val Asn Tyr Asn Gly
    175                 180                 185 gag atc acg gac ata cga gac ctt aga aag tcc agg ctg acc tgg acc         807
Glu Ile Thr Asp Ile Arg Asp Leu Arg Lys Ser Arg Leu Thr Trp Thr
190                 195                 200 acg cag ttg cac cgt cag ttc att gcg gca gtg aac cac ctc gga gaa         855
Thr Gln Leu His Arg Gln Phe Ile Ala Ala Val Asn His Leu Gly Glu
205             210                 215                 220 gac aag gca gtt cca aag aag ata cta ggg ata atg aag gtc aaa cat         903
Asp Lys Ala Val Pro Lys Lys Ile Leu Gly Ile Met Lys Val Lys His
            225                 230                 235 ttg aca aga gag caa gtt gcc agt cat ctg cag aaa tac agg atg caa         951
Leu Thr Arg Glu Gln Val Ala Ser His Leu Gln Lys Tyr Arg Met Gln
        240                 245                 250 ctg aag aaa tcg att cca aca aca agc aaa cac gga gcg act ttg tca         999
Leu Lys Lys Ser Ile Pro Thr Thr Ser Lys His Gly Ala Thr Leu Ser
    255                 260                 265 tcc acc gct ctc gac aaa aca caa gac cac cct tca aga tcg cag tat        1047
Ser Thr Ala Leu Asp Lys Thr Gln Asp His Pro Ser Arg Ser Gln Tyr
270                 275                 280 ttc aat caa gac gga tgc atg gaa atc atg gac tac tct tta ccg aga        1095
Phe Asn Gln Asp Gly Cys Met Glu Ile Met Asp Tyr Ser Leu Pro Arg
285             290                 295                 300 gat gac ctc tca agt ggc tca gag tgc atg ctt gaa gaa cag aac gat        1143
Asp Asp Leu Ser Ser Gly Ser Glu Cys Met Leu Glu Glu Gln Asn Asp
            305                 310                 315 tac tca tcc gaa ggt ttc caa gat ttc cga tgg gat tca gac aaa cag        1191
Tyr Ser Ser Glu Gly Phe Gln Asp Phe Arg Trp Asp Ser Asp Lys Gln
        320                 325                 330 gaa tat gga cca tgt ttt tgg aat ttc tag gtagagaata taatgatccc          1241
Glu Tyr Gly Pro Cys Phe Trp Asn Phe
    335                 340 atcatgtctc atgatccaca tccatatgtt gatacctgca attgactttc tgaataagtg      1301
aacattacca catccgtaaa a                                                1322

<210> SEQ ID NO 3
<211> LENGTH: 341
<212> TYPE: PRT
<213> ORGANISM: Oryza sativa

<400> SEQUENCE: 3

Met Asp His Arg Glu Leu Trp Pro Tyr Gly Leu Arg Val Leu Val Ile
1               5                   10                  15

Asp Asp Asp Cys Ser Tyr Leu Ser Val Met Glu Asp Leu Leu Leu Lys
                20                  25                  30

Cys Ser Tyr Lys Val Thr Thr Tyr Lys Asn Val Arg Glu Ala Val Pro
        35                  40                  45
```

```
Phe Ile Leu Asp Asn Pro Gln Ile Val Asp Leu Val Ile Ser Asp Ala
 50                  55                  60

Phe Phe Pro Thr Glu Asp Gly Leu Leu Ile Leu Gln Glu Val Thr Ser
 65                  70                  75                  80

Lys Phe Gly Ile Pro Thr Val Ile Met Ala Ser Ser Gly Asp Thr Asn
                 85                  90                  95

Thr Val Met Lys Tyr Val Ala Asn Gly Ala Ser Asp Phe Leu Leu Lys
            100                 105                 110

Pro Val Arg Ile Glu Glu Leu Ser Asn Ile Trp Gln His Ile Phe Arg
        115                 120                 125

Lys Gln Met Gln Asp His Lys Asn Asn Asn Met Val Gly Asn Leu Glu
130                 135                 140

Lys Pro Gly His Pro Pro Ser Ile Leu Ala Met Ala Arg Ala Thr Pro
145                 150                 155                 160

Ala Thr Thr Lys Ser Thr Ala Thr Glu Ala Leu Leu Ala Pro Leu Glu
                165                 170                 175

Asn Glu Val Arg Asp Asp Met Val Asn Tyr Asn Gly Glu Ile Thr Asp
            180                 185                 190

Ile Arg Asp Leu Arg Lys Ser Arg Leu Thr Trp Thr Gln Leu His
        195                 200                 205

Arg Gln Phe Ile Ala Ala Val Asn His Leu Gly Glu Asp Lys Ala Val
210                 215                 220

Pro Lys Lys Ile Leu Gly Ile Met Lys Val Lys His Leu Thr Arg Glu
225                 230                 235                 240

Gln Val Ala Ser His Leu Gln Lys Tyr Arg Met Gln Leu Lys Lys Ser
                245                 250                 255

Ile Pro Thr Thr Ser Lys His Gly Ala Thr Leu Ser Ser Thr Ala Leu
            260                 265                 270

Asp Lys Thr Gln Asp His Pro Ser Arg Ser Gln Tyr Phe Asn Gln Asp
        275                 280                 285

Gly Cys Met Glu Ile Met Asp Tyr Ser Leu Pro Arg Asp Asp Leu Ser
290                 295                 300

Ser Gly Ser Glu Cys Met Leu Glu Glu Gln Asn Asp Tyr Ser Ser Glu
305                 310                 315                 320

Gly Phe Gln Asp Phe Arg Trp Asp Ser Ala Lys Gln Glu Tyr Gly Pro
                325                 330                 335

Cys Phe Trp Asn Phe
            340

<210> SEQ ID NO 4
<211> LENGTH: 7576
<212> TYPE: DNA
<213> ORGANISM: Oryza sativa
<220> FEATURE:
<223> OTHER INFORMATION: genomic DNA
<220> FEATURE:
<221> NAME/KEY: CDS
<222> LOCATION: (1843)..(1951)
<220> FEATURE:
<221> NAME/KEY: CDS
<222> LOCATION: (3232)..(3384)
<220> FEATURE:
<221> NAME/KEY: CDS
<222> LOCATION: (5228)..(5629)
<220> FEATURE:
<221> NAME/KEY: CDS
<222> LOCATION: (5779)..(5855)
<220> FEATURE:
<221> NAME/KEY: CDS
```

-continued

<222> LOCATION: (6847)..(7131)

<400> SEQUENCE: 4

```
ggtacctatt tgttccatat ttttgctcga cattatccga gtttgtatcc atattcaaca      60
ctatccgtgt ttgatccgat tccgattata aaatatgggt taggatatgg gaagggtaag     120
atccgaccga acccgaccgg ttttcacccc tacacgtcgc taatctacac ttcgaggcaa     180
aaaaaaagag agagtaacaa atcaaactac aaaagcgcgc aatcgcatac acaataatta     240
aatttgtatc tatcgtcaca tatacaaata aaatttgatc ttgcatattt gcaccacaat     300
aaggtaaatac ctatgttttc tactttttag aaaatttatt aataactttt tttagataat     360
ttatgaataa ctatttggac cacaggaaat agacaacgta gtacgacaca ttctttccta     420
ggtcttatgt acgcatgatt gtgtgtatat tctcgacgac gccgacgacg gtgaccggtg     480
catatgttcc cagccgtcct ccgccgcgca ttgcggttgt ggaggaaggg agctccacgt     540
ctcgccatgg ccgtccacaa cctgagttag atctctagct acctgatccc caaaccctct     600
caaaagatg tatattcttc ctagcactct ggcccctgga ttagctcaaa aattcctcat     660
atatatgctg gctagctagc tgatagtata tactactcat aacccattct tcttccttac     720
ctagctagct agcaaacact gaagctggga gctctggcta tatgtccata tatatatata     780
ctacatcatt gctatagcta gctagctgga agaggaacat tcatacttaa ttctagttac     840
ttggagtgag tttaaaacac tgaattaggt gaaattgacc ggtggccgct gactgctggc     900
aggctagctt tggtgattaa ttaattatct ctcggagtaa gtcttctatt tgatatcaca     960
tgcatggaag aaggtatata tgtctacgcc aacattcatg tacttagtcc tctactattt    1020
ctacatagtt aattacaacc caccattaac tgtattagtt acttagaact ctcacattta    1080
accacgtcat gatcatatca acggtgttat ccatcaattg aggtgtgtcg tctatgagat    1140
atcagcaatt aattaagatc aacatttctc agcaaaggag ctttaaaacc ctgctgcaaa    1200
tatgcagggg tacgtatcca aatatatcat atacccctgt cgtatatagt atttacatgt    1260
agttattgat gatgatagat tgctcatgca tggaggtgat tatttcttgt gtgtttggtt    1320
tgttttcct ggaaatagct atagctttgc acatatatat agctgcttaa atattcttga    1380
atgcagacat acgagttttc gatatatact cagatatatt agtacaatat tattatttgt    1440
atgcatatca tcagtgactc gattgatatt tgaagatata tacttatata aaaatgcaag    1500
gatatatgca tgaagaacat gtccatatat atatatatat agagagagag agagatctgt    1560
gtctagcttg cactacacca tatatatata tatataacct accttagcca aaggagtcag    1620
ttattaactg tagttagcat tattgttgaa ttaatgctat acctcattaa ctatatatgg    1680
tgcacgcgca ttccatgcat catgcatgtt tattactcgt catatattat atacgatgta    1740
aacacaaagt acaattgatt atattatttt taatttattt tttaaaaacg gagaagcaga    1800
tgtagtcgtt aattttttgtt ttctcctaat taggttaaa ta atg gat cac cga       1854
                                              Met Asp His Arg
                                                1
gag ctg tgg cct tat gga cta aga gtt ctg gtc atc gat gac gac tgt      1902
Glu Leu Trp Pro Tyr Gly Leu Arg Val Leu Val Ile Asp Asp Asp Cys
  5                  10                  15                  20
tca tac ttg tca gtc atg gaa gat tta ctt ctg aag tgc agc tac aag g   1951
Ser Tyr Leu Ser Val Met Glu Asp Leu Leu Leu Lys Cys Ser Tyr Lys
                 25                  30                  35
gtaaaatac catctataca agacacataa ttaattaaca aaatctaact atctagcttg     2010
gcatatatag tgatcgaata tattgatgcg aattaagatt atataagatt atacatataa    2070
```

```
aatattgagt ttttctggat taaatagaag atgcatacag aagttacaaa cacgcaccac    2130
tacacacgtg tccatgcaca ctaatgtgtc tcctaatata tacatgctca gatacgctca    2190
gatagacaga tcagatcaat ggcaaatctt tgacctcact aaaatcctat tggaagtatg    2250
tgcataaaat ttgtaaataa aatttgtata agatcattaa tttttctact atttaagttc    2310
agtcagtttc acatgcataa tacatgataa tcctatatta tgtatatata tcattccatg    2370
cttactttaa ccaaattttc cctctacctt ggtgtagcca atgcatcatt tagttataat    2430
atgttatgaa tacataaata tatagcagaa tttatgttca ttgtcacata aaatgtgttt    2490
gcatgattct tattattaaa ataaatattt ggtaatgtgt ttcagctaac aggcacatgg    2550
aatatagtca aagatgatca gctctgtggt tggactgcca tttgctttga agaagctaca    2610
aaaatttaat taattttgaa aatgaaataa aacatgcggg agttctatat agtgtatata    2670
ccttaaaata attcttttct ttcttcccat ttagtttgtc aaattagact gcaagtagta    2730
attaaatcga agtcttggag ggtagtgcag aacatatatt aagaacaaag gtatacttta    2790
attatatatc ctcaccttgc agttgcggtt tctagggtta gcatatattt tgtgaggtgt    2850
caactcagat attgtgatga caaattaacc tataaatttt ctccatatgt ttttattcaa    2910
tgggcgatcc atactccata aaatgcatat taattaattt gtaatgaaaa accgggaaaa    2970
gttgtgttcg tatatatacc aagaatcttg caagaaagtg attgtatgta gtaacatttc    3030
catacacaca tgaagttaca cacacacaca cacacacaca cacacttata tatatatata    3090
tatatatata tatatatata tatatatata tatatagtct aacgtcaaaa atgaaattct    3150
tctagatata tcttacaaat attcgatatt ggcctcattt tctttgtgat gtatgtacct    3210
tatattagta ttctcttgta g tt aca acg tat aag aac gtc aga gaa gct       3260
                        Val Thr Thr Tyr Lys Asn Val Arg Glu Ala
                                40                  45
gtg cct ttc ata ttg gac aat cca caa ata gtt gac cta gta atc agt      3308
Val Pro Phe Ile Leu Asp Asn Pro Gln Ile Val Asp Leu Val Ile Ser
        50                  55                  60
gat gcg ttc ttt cct acc gaa gat ggt ttg ctc att ctg caa gaa gta      3356
Asp Ala Phe Phe Pro Thr Glu Asp Gly Leu Leu Ile Leu Gln Glu Val
 65                  70                  75
acc tcc aag ttt ggc ata cct aca gtg a gtaagtaat ttatttata             3403
Thr Ser Lys Phe Gly Ile Pro Thr Val
    80                  85
tctccttaca cattcttact agtttatatg gattgcacgc cttaacttat gcgtgcgtgt    3463
gtgcttgagg aactaggtca aatatgcact aatatataat aagctattca ctccgtctca    3523
aaatataact actttcgcta cgcgcgggtc aggtcatctg tgatgggccc aaaccgtacc    3583
tctgacaggt ttggccctca tcagagatta gtggtcagcc tactcacctc tgacgggccg    3643
ttagaaatgg gtcgtcacag gtgactcact tgtgacgtgt ggctcttttcc aacatgtcag    3703
aggtgactgt caccttttgac gggttgtatt ttatcactta tcacaggtgt gaaaaaacaa    3763
cccaaaagaa aaagcaaaag ccctcagccc aagctcacg ccaagagcat aacacaaacat    3823
ctttgcattt tattggcaga tctgataaca tccaagaaaa aactacagat gaaacaaaag    3883
atgtatgata catatcaaac ttgagtaaca atatacatca cacaagtaat gatctccatc    3943
ctaacaaact acacatccac acaagtaaca aagaatatgg cccaatctga aatttggcag    4003
tgaacatttg caagatatga aatcaagaac aacctacagg agtgtcaagg tcagggaggc    4063
cgccgtgctc cccctccacc cctgtcagat ctacccacca actccaccac cagatctacc    4123
```

-continued

```
aatcctccag ggtcagagag gccagatcca cgctcgagga gagcctagat ccgcacttgt    4183
gataaggacg gctaccattg ctttggactg gagaagacga ggaaatggca tcaatgatcg    4243
gggaggctag atctgctccc gaggaggcag ctggtgcttg agggtagagg agacagcggc    4303
caacagtcgg atcgatccat gtcccccgac cttgtggagg ctagatccca cggtcgccgg    4363
atgctggcag atgggggaa gcccgggctc gggggagagg ccggctccgg tggccagcgg    4423
atgggtgata aggaggagg cggccaacag tcaaggaga ggccgcggcg gccggtgatt    4483
gggggaagga ggacgcaacg gctggtgatc agggaaagga ggaggcggta gccgaatcca    4543
cgtcctggag gcaagatccg acgaccggtg atcaggaggc ggttagggga agagagtttg    4603
agatatgggg ataaggatga gagggagaaa gtgagcagat gtgaggagaa gaaagaagag    4663
agaccggagg atgggaggag atgggaaggg agttgggcca tacacatggg gattggggga    4723
ttttccttta ttttaaatta tcattgacga gcataagaat ttaacacgtt agatatgagg    4783
tatcacatca tgtgatgagg tgcaaactca acacccgtca cagatagaag gtcatatatg    4843
acgggcctat atgtgggccc gtcaaagatg ttatgtgtct agtcctcata aatgtccgta    4903
agatgagttt ttacttgtga cgagccatcc ctttgaaccc catctacaac tggctatagt    4963
tcaaccccat cagaaataat atctttcgtg acgagacatt ggcccgtcac agatatgccg    5023
tcacaatggg ctgctctagt gaagtgttcg agaattcaaa ttcgtctcaa ccaatcacaa    5083
tcatttaatt tattcaccta ttcttttat ctcaaccaat cgcaatcatt tttttataaa    5143
tagcaatatt ttgagacaaa aggatcggag tacaccctaa taagttcact cacaaggaaa    5203
ctttatatat gttttttta ctag tt atg gct tca agt gga gac aca aat aca     5256
                          Ile Met Ala Ser Ser Gly Asp Thr Asn Thr
                                       90                 95 gtg atg aaa tat gtt gca aat ggc gct ttt gat ttc ctg cta aaa cct       5304
Val Met Lys Tyr Val Ala Asn Gly Ala Phe Asp Phe Leu Leu Lys Pro
            100                 105                 110 gtg agg atc gaa gag ctg agc aac att tgg cag cac ata ttc cga aag       5352
Val Arg Ile Glu Glu Leu Ser Asn Ile Trp Gln His Ile Phe Arg Lys
    115                 120                 125 caa atg caa gat cac aag aac aat aac atg gtt gga aat ctc gaa aaa       5400
Gln Met Gln Asp His Lys Asn Asn Asn Met Val Gly Asn Leu Glu Lys
130                 135                 140                 145 ccc ggt cat cct cca tca ata tta gcc atg gct cgt gct act ccg gct       5448
Pro Gly His Pro Pro Ser Ile Leu Ala Met Ala Arg Ala Thr Pro Ala
                150                 155                 160 acc acc aga tca acg gcc acc gaa gct tcg cta gcg cct cta gaa aat       5496
Thr Thr Arg Ser Thr Ala Thr Glu Ala Ser Leu Ala Pro Leu Glu Asn
            165                 170                 175 gag gtg aga gat gac atg gtc aac tac aat ggc gag atc acg gac ata       5544
Glu Val Arg Asp Asp Met Val Asn Tyr Asn Gly Glu Ile Thr Asp Ile
    180                 185                 190 cga gac ctc gga aag tcc agg ctg acc tgg acc acg cag ttg cac cgt       5592
Arg Asp Leu Gly Lys Ser Arg Leu Thr Trp Thr Thr Gln Leu His Arg
195                 200                 205 cag ttc att gca gca gtg aac cac ctc gga gaa gac a gtgagtgat          5638
Gln Phe Ile Ala Ala Val Asn His Leu Gly Glu Asp
210                 215                 220 caaattaaac ttctttgcag taccatttca atcactttc atatgtatac atgcgtgtat     5698
acattaattt taatttacta gtatatatgt atttcctagc ttgttttaag atgtggtaat    5758
tatgtgtaat ttatttgcag ag gca gtt cca aag aag ata cta ggg ata atg     5810
                         Lys Ala Val Pro Lys Lys Ile Leu Gly Ile Met
                                     225                 230
```

```
aag gtc aaa cat ttg aca aga gag caa gtt gcc agt cat ctg cag      5855
Lys Val Lys His Leu Thr Arg Glu Gln Val Ala Ser His Leu Gln
    235                 240                 245 gtaatatttc agtggctcat tgcaagatga aagcaaaacc tatcatgttt ttcctttcaa  5915
gatttcttta cgataaatta gaccatatgc aagatatata aagggcaaa ttccctccag   5975 agttttaga aaacactttc caatgtataa atgtaaaaa tgtgttgtcc atgttacaat    6035
gattcttaat tatgctactt tcacaattgt acatataaat tagcctaata ctactcatac  6095
atatgtatca ggtacacatt gtaagtttat atattttcat cactctaatg tactccctag  6155
ctctgtccat gaatacaagg gattataccc aattaagaag aaactaagaa agtgggtaaa  6215
gtacgcactg ctgctcatga tggagtatta ctagtagtac attctctcta ttttttttggg 6275 tagggatgat ggggagtagt gctagtagat ttttttttct cttttttat agaaccgatg   6335 gggtaaataa atgaagctg ctggtatatg aattactgac tattgttctc tttgctttcc   6395
caatacttat attcttgata aactagaggc agggtttgaa atttcgaaat tggatttat   6455 gtcgggggtg aacgaaatta ccgaaaattt ctggccggaa ttatttgaaa atttgactga  6515
atttgaataa aatttgacta aattcacaaa aaaattgcaa aaaaactgaa aattttaggc  6575
gagatttgag catgccggtg gagggcaaaa ttaccaaaat ttcggaaaat tcgaaccgaa  6635
atttcaaacc ctgactagag gatcataatc atatttatgg acagagggag catgaatgaa  6695
tatgaccgat gcttctaggg tttccttcta cagcatccta attagcttat tcaagttaga  6755
gtgcatccac tgcataactt ctttcgctgc ttcttcagct aattcagttg aacatatata  6815
accataaaac ctaacatttg aactgatgca g aaa tac agg atg caa ctg aag    6867
                                  Lys Tyr Arg Met Gln Leu Lys
                                                            250 aaa tcg att cca aca aca agc aaa cac gga gcg act ttg tca tcc acc   6915
Lys Ser Ile Pro Thr Thr Ser Lys His Gly Ala Thr Leu Ser Ser Thr
255                 260                 265                 270 gct ctc gac aaa aca caa gac cac cct tca aga tcg cag tat ttc aat   6963
Ala Leu Asp Lys Thr Gln Asp His Pro Ser Arg Ser Gln Tyr Phe Asn
                275                 280                 285 caa gac gga tgc atg gaa atc atg gac tac tct tta ccg aga gat gac   7011
Gln Asp Gly Cys Met Glu Ile Met Asp Tyr Ser Leu Pro Arg Asp Asp
            290                 295                 300 ctc tca agt ggc tca gag tgc atg ctt gaa gaa ctg aac gat tac tca   7059
Leu Ser Ser Gly Ser Glu Cys Met Leu Glu Glu Leu Asn Asp Tyr Ser
        305                 310                 315 tcc gaa ggt ttc caa gat ttc cga tgg gat tca gac aaa cag gaa tat   7107
Ser Glu Gly Phe Gln Asp Phe Arg Trp Asp Ser Asp Lys Gln Glu Tyr
    320                 325                 330 gga cca tgt ttt tgg aat ttc tag gtagagaata taatgatccc atcatgtctc  7161
Gly Pro Cys Phe Trp Asn Phe
335                 340 atgatccaca tccatatgtt gatacctgca attgactttc tgaataagtg aacattacca  7221
catccatata tactcttgat gttcattgca gaactaaact gacaacatac tgtacatagg  7281
ttgtctactc tatctagatg tgtcacatgc aaagattata ttgataacat tcatccaaat  7341
caatgtccat cctctcaatt atgggtgtgt ttggggaagt tttagattct gagaagttgc  7401
tgaagataat acatgcatct aggtggcgac aatctagaga tgtcgaggaa accaactttt  7461
ggcttatagt tcattttttg gattttacga ctacaatttc ctaaaatata gacgaaaagc  7521
tatatattcc tacatataag atccgtaatc acaaaaaaaa acaatatatg gatcc       7576
```

```
<210> SEQ ID NO 5
<211> LENGTH: 1026
<212> TYPE: DNA
<213> ORGANISM: Oryza sativa
<220> FEATURE:
<221> NAME/KEY: CDS
<222> LOCATION: (1)..(1026)

<400> SEQUENCE: 5 atg gat cac cga gag ctg tgg cct tat gga cta aga gtt ctg gtc atc        48
Met Asp His Arg Glu Leu Trp Pro Tyr Gly Leu Arg Val Leu Val Ile
 1               5                  10                  15 gat gac gac tgt tca tac ttg tca gtc atg gaa gat tta ctt ctg aag        96
Asp Asp Asp Cys Ser Tyr Leu Ser Val Met Glu Asp Leu Leu Leu Lys
            20                  25                  30 tgc agc tac aag gtt aca acg tat aag aac gtc aga gaa gct gtg cct       144
Cys Ser Tyr Lys Val Thr Thr Tyr Lys Asn Val Arg Glu Ala Val Pro
        35                  40                  45 ttc ata ttg gac aat cca caa ata gtt gac cta gta atc agt gat gcg       192
Phe Ile Leu Asp Asn Pro Gln Ile Val Asp Leu Val Ile Ser Asp Ala
    50                  55                  60 ttc ttt cct acc gaa gat ggt ttg ctc att ctg caa gaa gta acc tcc       240
Phe Phe Pro Thr Glu Asp Gly Leu Leu Ile Leu Gln Glu Val Thr Ser
65                  70                  75                  80 aag ttt ggc ata cct aca gtg att atg gct tca agt gga gac aca aat       288
Lys Phe Gly Ile Pro Thr Val Ile Met Ala Ser Ser Gly Asp Thr Asn
                85                  90                  95 aca gtg atg aaa tat gtt gca aat ggc gct ttt gat ttc ctg cta aaa       336
Thr Val Met Lys Tyr Val Ala Asn Gly Ala Phe Asp Phe Leu Leu Lys
            100                 105                 110 cct gtg agg atc gaa gag ctg agc aac att tgg cag cac ata ttc cga       384
Pro Val Arg Ile Glu Glu Leu Ser Asn Ile Trp Gln His Ile Phe Arg
        115                 120                 125 aag caa atg caa gat cac aag aac aat aac atg gtt gga aat ctc gaa       432
Lys Gln Met Gln Asp His Lys Asn Asn Asn Met Val Gly Asn Leu Glu
    130                 135                 140 aaa ccc ggt cat cct cca tca ata tta gcc atg gct cgt gct act ccg       480
Lys Pro Gly His Pro Pro Ser Ile Leu Ala Met Ala Arg Ala Thr Pro
145                 150                 155                 160 gct acc acc aga tca acg gcc acc gaa gct tcg cta gcg cct cta gaa       528
Ala Thr Thr Arg Ser Thr Ala Thr Glu Ala Ser Leu Ala Pro Leu Glu
                165                 170                 175 aat gag gtg aga gat gac atg gtc aac tac aat ggc gag atc acg gac       576
Asn Glu Val Arg Asp Asp Met Val Asn Tyr Asn Gly Glu Ile Thr Asp
            180                 185                 190 ata cga gac ctc gga aag tcc agg ctg acc tgg acc acg cag ttg cac       624
Ile Arg Asp Leu Gly Lys Ser Arg Leu Thr Trp Thr Thr Gln Leu His
        195                 200                 205 cgt cag ttc att gca gca gtg aac cac ctc gga gaa gac aag gca gtt       672
Arg Gln Phe Ile Ala Ala Val Asn His Leu Gly Glu Asp Lys Ala Val
    210                 215                 220 cca aag aag ata cta ggg ata atg aag gtc aaa cat ttg aca aga gag       720
Pro Lys Lys Ile Leu Gly Ile Met Lys Val Lys His Leu Thr Arg Glu
225                 230                 235                 240 caa gtt gcc agt cat ctg cag aaa tac agg atg caa ctg aag aaa tcg       768
Gln Val Ala Ser His Leu Gln Lys Tyr Arg Met Gln Leu Lys Lys Ser
                245                 250                 255 att cca aca aca agc aaa cac gga gcg act ttg tca tcc acc gct ctc       816
Ile Pro Thr Thr Ser Lys His Gly Ala Thr Leu Ser Ser Thr Ala Leu
            260                 265                 270
```

```
gac aaa aca caa gac cac cct tca aga tcg cag tat ttc aat caa gac      864
Asp Lys Thr Gln Asp His Pro Ser Arg Ser Gln Tyr Phe Asn Gln Asp
            275                 280                 285 gga tgc atg gaa atc atg gac tac tct tta ccg aga gat gac ctc tca      912
Gly Cys Met Glu Ile Met Asp Tyr Ser Leu Pro Arg Asp Asp Leu Ser
290                 295                 300 agt ggc tca gag tgc atg ctt gaa gaa ctg aac gat tac tca tcc gaa      960
Ser Gly Ser Glu Cys Met Leu Glu Glu Leu Asn Asp Tyr Ser Ser Glu
305                 310                 315                 320 ggt ttc caa gat ttc cga tgg gat tca gac aaa cag gaa tat gga cca     1008
Gly Phe Gln Asp Phe Arg Trp Asp Ser Asp Lys Gln Glu Tyr Gly Pro
                325                 330                 335 tgt ttt tgg aat ttc tag                                             1026
Cys Phe Trp Asn Phe
                340

<210> SEQ ID NO 6
<211> LENGTH: 341
<212> TYPE: PRT
<213> ORGANISM: Oryza sativa

<400> SEQUENCE: 6

Met Asp His Arg Glu Leu Trp Pro Tyr Gly Leu Arg Val Leu Val Ile
  1               5                  10                  15

Asp Asp Asp Cys Ser Tyr Leu Ser Val Met Glu Asp Leu Leu Leu Lys
             20                  25                  30

Cys Ser Tyr Lys Val Thr Thr Tyr Lys Asn Val Arg Glu Ala Val Pro
         35                  40                  45

Phe Ile Leu Asp Asn Pro Gln Ile Val Asp Leu Val Ile Ser Asp Ala
     50                  55                  60

Phe Phe Pro Thr Glu Asp Gly Leu Leu Ile Leu Gln Glu Val Thr Ser
 65                  70                  75                  80

Lys Phe Gly Ile Pro Thr Val Ile Met Ala Ser Ser Gly Asp Thr Asn
                 85                  90                  95

Thr Val Met Lys Tyr Val Ala Asn Gly Ala Phe Asp Phe Leu Leu Lys
            100                 105                 110

Pro Val Arg Ile Glu Glu Leu Ser Asn Ile Trp Gln His Ile Phe Arg
        115                 120                 125

Lys Gln Met Gln Asp His Lys Asn Asn Asn Met Val Gly Asn Leu Glu
    130                 135                 140

Lys Pro Gly His Pro Pro Ser Ile Leu Ala Met Ala Arg Ala Thr Pro
145                 150                 155                 160

Ala Thr Thr Arg Ser Thr Ala Thr Glu Ala Ser Leu Ala Pro Leu Glu
                165                 170                 175

Asn Glu Val Arg Asp Asp Met Val Asn Tyr Asn Gly Glu Ile Thr Asp
            180                 185                 190

Ile Arg Asp Leu Gly Lys Ser Arg Leu Thr Trp Thr Gln Leu His
        195                 200                 205

Arg Gln Phe Ile Ala Ala Val Asn His Leu Gly Glu Asp Lys Ala Val
    210                 215                 220

Pro Lys Lys Ile Leu Gly Ile Met Lys Val Lys His Leu Thr Arg Glu
225                 230                 235                 240

Gln Val Ala Ser His Leu Gln Lys Tyr Arg Met Gln Leu Lys Lys Ser
                245                 250                 255

Ile Pro Thr Thr Ser Lys His Gly Ala Thr Leu Ser Thr Ala Leu
            260                 265                 270
```

```
Asp Lys Thr Gln Asp His Pro Ser Arg Ser Gln Tyr Phe Asn Gln Asp
        275                 280                 285

Gly Cys Met Glu Ile Met Asp Tyr Ser Leu Pro Arg Asp Asp Leu Ser
        290                 295                 300

Ser Gly Ser Glu Cys Met Leu Glu Glu Leu Asn Asp Tyr Ser Ser Glu
305                 310                 315                 320

Gly Phe Gln Asp Phe Arg Trp Asp Ser Asp Lys Gln Glu Tyr Gly Pro
                325                 330                 335

Cys Phe Trp Asn Phe
            340

<210> SEQ ID NO 7
<211> LENGTH: 7540
<212> TYPE: DNA
<213> ORGANISM: Oryza sativa
<220> FEATURE:
<223> OTHER INFORMATION: genomic DNA
<220> FEATURE:
<221> NAME/KEY: CDS
<222> LOCATION: (1850)..(1958)
<220> FEATURE:
<221> NAME/KEY: CDS
<222> LOCATION: (3219)..(3371)
<220> FEATURE:
<221> NAME/KEY: CDS
<222> LOCATION: (5212)..(5613)
<220> FEATURE:
<221> NAME/KEY: CDS
<222> LOCATION: (5763)..(5839)
<220> FEATURE:
<221> NAME/KEY: CDS
<222> LOCATION: (6811)..(7095)

<400> SEQUENCE: 7
ggtacctatt tgttccatat ttttgctcga cattatctga gtttgtatcc atattcaaca      60
ctatccgtgt ttgatccgat tccaattata aaatatgggt taggatatgg gaagggtaag     120
atccgaccga acccgacccg ttttcacccc tacacgtcgc taatctacac ttcgaggcaa     180
aaaaaaaaga gagtaacaaa tcaaactaca aaagcgcgca atcgcataca caataattaa     240
atttgtatct atcgtcacat atacaaataa aatttgatct tgcatatttg caccacaata     300
aggtaatacc tatgttttct acttttttaga aaatttatta ataactttttt ttagataatt     360 tatgaataac tatttggacc acaggaaata gacaacgtag tacgacacat tctttcctag     420
gtcttatgta cgcatgattg tgtgtatatt ctcgcctacg ccgacgacgg tgaccggtgc     480
atatgttccc agccgtcctc cgccgcgcat tgcggttgtg gaggaaggga gctccacgtc     540
tcgccatggc cgtccacaac ctgagttaga tctctagcta cctgatcccc aaaccctctc     600
aaaaagatgt atattcttcc tagcactctg gcccctggat tagctcaaaa attcctcata     660
tatatgctgg ctagctagct gatagtatat actactcata acccattctt cttccttacc     720
tagctagcta gcaaacactg aagctgggag ctctggctat atgtccatat atatatatat     780
actacatcat tgctatagct agctagctgg aggaggaaca ttcatactta attctagtta     840
cttggagtga gtttaaaaca ctgaattagg tgaaattgac cggtggccgc tgactgctgg     900
caggctagct ttggtgatta attaattatc tgtcggagta agtcttatac ttgatattac     960
atgcatggaa gaaggtatat atgtctacgc caacattcat gtacttagtc ctctactatt    1020
tctacatagt taattacaac ccaccattaa ctgtattaat tacttagaac tctcacattt    1080
aaccacgtca tgatcatatc aacggtgtta tccatcaatt gaggtgtgtc gtctatgaga    1140
tatcagcaat taattaagat caacatttct cagcaaagga gctttaaaac cctgctgcaa    1200
```

-continued

```
atatgcaggg gtacgtatcc aaatatatca tatacccctg tcgtatatag tatttacatg    1260
tagttattga tgatgataga ttgctcatgc atggaggtga ttatttcttg tgtgtttggt    1320
ttgttttgcc tggaaatagc tatagctttg cacatatagc tgcttaaata ttcttgaatg    1380
cagacatacg agttttcgat atatactcag atatattagt acaatattat tatttgtatg    1440
catatcatca gtgactcgat tgatatttga agatatatac ttatataaaa atgcaaggat    1500
atatgcatga agaacatgtc catatatata tatatatata tatatagaga gagagagaga    1560
gagagatctg tgtctagctt gcactacacc atatatatat ataacctacc ttagccaaag    1620
gagtcagtta ttaactgtag ttagcattat tgttgaatta atgctatacc tcattaacta    1680
tatatggtgc acgcgcattc catgcatcat gcatgtttat tactcgtcat atattatata    1740
cgatgtaaac acaaagtaca attgattata ttattgttaa ttattttttt aaaaacggag    1800
aagcagatgt agtcgttaat ttttgttttc tcctaattag gttataata atg gat cac    1858
                                                  Met Asp His
                                                    1 cga gag ctg tgg cct tat gga cta aga gtt ctg gtc atc gat gac gac    1906
Arg Glu Leu Trp Pro Tyr Gly Leu Arg Val Leu Val Ile Asp Asp Asp
  5              10                  15 tgt tca tac ttg tca gtc atg gaa gat tta ctt ctg aag tgc agc tac    1954
Cys Ser Tyr Leu Ser Val Met Glu Asp Leu Leu Leu Lys Cys Ser Tyr
 20              25                  30              35 aag g gtaaaatac catctataca agacacataa ttaattaaca aaatctaact           2007
Lys atctagcttg gcatatatag tgatcgaata tattgatgcg aattaagatt atataagatt    2067
atacatataa aatattgagt ttttctggat taaatagaag atgcatacag aagttacaaa    2127
cacgcaccac tacacacgtg tccatgcaca ctaatgtgtc tcctaatata tacatgctca    2187
gatacgctca gatagacaga tcagatcaat ggcaaatctt tgacctcact aaaatccctat   2247 tggaagtatg tgcataaaat ttgtaaataa aatttgtata agatcattaa ttttttctact   2307 atttaagttc agtcagtttc acatgcataa tacatgataa tcctatatta tgtatatata    2367
tcattccatg cttactttaa ccaaattttc cctctaccct ggtgtagcca atgcatcata    2427
tagttataat atgttatgaa tacataaata tatagcagaa tttatgttca ttgtcacata    2487
aaatgtgttt gcatgattct tattattaaa ataaatattt ggtaatgtgt ttcagctaac    2547
aggcacatgg aatatagtca agatgatca gctctgtggt tggactgcca tttgctttga     2607
agaagctaca aaaatttaat taattttgaa aatgaaataa aacatgcggg agttctatat    2667
agtgtatata ccttaaaata attcttttct ttcttcccat ttagtttgtc aaattagact    2727
gcaagtagta attaaatcga agtcttggag ggtagtgcag aacatatatt aagaacaaag    2787
gtatacttta attatatatc ctcaccttgc agttgcggtt tctagggtta gcatatattt    2847
tgtgaggtgt caactcagat attgtgatga caaattaacc tataaatttt ctccatatgt    2907
ttttattcaa tgggcgatcc atactccata aaatgcatat taattaattt gtaatgaaaa    2967
ccgggaaaag ttgtgttcgt atatatacca agaatcttgc aagaaagtga ttgtatgtag    3027
taacatttcc atacacacat gaagttacac acacacacac acacatatta tatatatata    3087
tatatatata tatatatata tatatagtct aacgtcaaaa atgaaattct tctagatata    3147
tcttacaaat attcgatatt ggcctcattt tctttgtgat gtatgtacct tatattagta    3207
ttctcttgta g tt aca acg tat aag aac gtc aga gaa gct gtg cct ttc     3256
             Val Thr Thr Tyr Lys Asn Val Arg Glu Ala Val Pro Phe
                                 40                  45
```

```
ata ttg gac aat cca caa ata gtt gac cta gta atc agt gat gcg ttc    3304
Ile Leu Asp Asn Pro Gln Ile Val Asp Leu Val Ile Ser Asp Ala Phe
 50                  55                  60                  65 ttt cct acc gaa gat ggt ttg ctc att ctg caa gaa gta acc tcc aag    3352
Phe Pro Thr Glu Asp Gly Leu Leu Ile Leu Gln Glu Val Thr Ser Lys
             70                  75                  80 ttt ggc ata cct aca gtg a gtaagtaat ttatttatta tctccttaca          3400
Phe Gly Ile Pro Thr Val
             85 cattcttact agtttatatg gattacacgc cttaacttat gcgtgcgtgt gtgcttgagg  3460
aactaggtca aatatgcact aatatataat aagctactca ctccgtctca aaatataact  3520
actttcgcta cgcgcgggtc aggtcatctg tgatgggccc aaaccgtacc tctgacaggt  3580
tcggccctca tcagagatta gtggtcagcc tactcacctc tgacgggccg ttagaaatgg  3640
gtcgtcacag gtgactcact tgtgatgtgt ggctctttcc aacatgtcag aggtgactgt  3700
caccctttgac gggttgtatt ttatcactta tcacaggtgt gaaaaaacaa cccaaaagaa  3760
aaagcaaaag ccctcagccc caagctcacg ccaagagcat aacacaacat ctttgcattt  3820
tattggcaga tctgataaca tccaagaaaa aactacagat gaaacaaaag atgtatgata  3880
catatcaaac ttgagtaaca atatacatca cacaagtaat gatctccatc ctaacaaact  3940
acacatccac acaagtaaca aagaatatgg cccaatctga aatttggcag tgaacatttg  4000
cagatatgaa atcaagaaca acctacagga gtgtcaaggt cagggaggcc gccgtgctcc  4060
ccctccaccc ctgtcagatc tacccaccaa ctccaccacc agatctgcca atcctccagg  4120
gtcagagagg ctagatccac gctcgaggag agcctagatc cgcacttgtg atagggacgg  4180
ctaccattgc tttggactgg agaagacgag gaaatggcat caatgatcgg ggaggctaga  4240
tctgcacccg aggaggcagc tggtgcttga gggtagagga gacagcggcc aacagtcgga  4300
tcgatccatg tccccccgacc ttgtggaggc tagatcccac ggtcgccgga tgctggcgga  4360
gatgggggag cccgggctcg ggggagaggc cggctccggt ggccggcggt tgggtgataa  4420
aggaggaggc ggccaacagt caagggagag gccgcggcgg ccgtgattg ggggaaggag   4480
gacgcaacgg ctggagatcg gggaaaggag gaggcggtag ccgaatccac atcctggagg  4540
caagatccgg cgaccggtga tcaggaggcg gttaggggaa gagagtttga gatatgggga  4600
taaggatgag agggagaaag tgagcagatg tgaggagaag aaagaagaga gaccggagga  4660
tgggaggaga tgggaaggga gttgggccgt acacatgggg attgggggat tttcctttat  4720
tttaaattat cattgacgag cataagaatt taacacgtta gatatgaggt atcacatcct  4780
gtgatgaggt gcaaactcaa cacccgtcac agatagaagg tcatatatga cgggcctata  4840
tgtgggcccg tcaaagatgt tatgtgtcga gtcctcataa atgtccgtaa gatgagtttt  4900
tacttgtgac gagccatccc tttgaacccc atctacaact ggctatagtt caaccctatc  4960
agaaataata tctttcgtga cgagacattg gcctgtcaca gatatgccgt cacaatgggc  5020
tgctctagtg aagtgttcga gaattcaaat tcgtctcaac caatcacaat catttaattt  5080
attcacctat ttttttatct caaccaatcg caatcatttt tttataaata gtaatatttt  5140
gagacaaaag gatcggagta cacccctaata agtttactca caaggaaact ttatatatgt  5200
tttttaacta g tt atg gct tca agt gga gac aca aat aca gtg atg aaa   5249
              Ile Met Ala Ser Ser Gly Asp Thr Asn Thr Val Met Lys
                   90                  95                 100 tat gtt gca aat ggc gct ttt gat ttc ctg cta aaa cct gtg agg atc    5297
Tyr Val Ala Asn Gly Ala Phe Asp Phe Leu Leu Lys Pro Val Arg Ile
```

|     |     |
| --- | --- |
| <pre>                        105                 110                     115
     gaa gag ctg agc aac att tgg cag cac ata ttc cga aag caa atg caa
     Glu Glu Leu Ser Asn Ile Trp Gln His Ile Phe Arg Lys Gln Met Gln
                     120                 125                 130</pre> | 5345 |
| <pre>     gat cac aag aac aat aac atg gtt gga aat ctc gaa aaa ccc ggt cat
     Asp His Lys Asn Asn Asn Met Val Gly Asn Leu Glu Lys Pro Gly His
                 135                 140                 145</pre> | 5393 |
| <pre>     cct cca tca ata tta gcc atg gct cgt gct act ccg gct acc acg aga
     Pro Pro Ser Ile Leu Ala Met Ala Arg Ala Thr Pro Ala Thr Thr Arg
             150                 155                 160</pre> | 5441 |
| <pre>     tca acg gcc acc gaa gct tcg cta gcg cct cta gaa aat gag gtg aga
     Ser Thr Ala Thr Glu Ala Ser Leu Ala Pro Leu Glu Asn Glu Val Arg
     165                 170                 175                 180</pre> | 5489 |
| <pre>     gat gac atg gtc aac tac aat ggc gag atc acg gac ata cga gac ctc
     Asp Asp Met Val Asn Tyr Asn Gly Glu Ile Thr Asp Ile Arg Asp Leu
                     185                 190                 195</pre> | 5537 |
| <pre>     gga aag tcc agg ctg acc tgg acc acg cag ttg cac cgt cag ttc att
     Gly Lys Ser Arg Leu Thr Trp Thr Thr Gln Leu His Arg Gln Phe Ile
                 200                 205                 210</pre> | 5585 |
| <pre>     gca gca gtg aac cac ctc gga gaa gac a gtgagtgat caaattaaac
     Ala Ala Val Asn His Leu Gly Glu Asp
             215                 220</pre> | 5632 |
| ttctttgcag taccatttca atcactttc atatgtatac atgcgtgtat acattaattt | 5692 |
| taatttacta gtatatatgt atttcctagc ttgttttaag atgtggtaat tatgtgtaat | 5752 |
| <pre>ttatttgcag ag gca gtt cca aag aag ata cta ggg ata atg aag gtc aaa
          Lys Ala Val Pro Lys Lys Ile Leu Gly Ile Met Lys Val Lys
               225                 230                 235</pre> | 5803 |
| <pre>cat ttg aca aga gag caa gtt gcc agt cat ctg cag gtaatatttc
His Leu Thr Arg Glu Gln Val Ala Ser His Leu Gln
         240                 245</pre> | 5849 |
| agtggctcat tgcaagatga aagcaaaacc tatcatgttt ttcctttcaa gatttcttta | 5909 |
| cgataaatta gaccatatgc aagatatata caagggcaaa ttccctccag agttttaga | 5969 |
| aaacactttc caatgtataa tatgtaaaaa tgtgttgtcc atgttacaat gattcttaat | 6029 |
| tatactactt tcacaattgt acatataaat tagcctaata ctactcatac atatgtatca | 6089 |
| ggtacacatt gtaagtttat atatttgcat cactctaatg tactccctag ctctgtccat | 6149 |
| gaatacaagg gattataccc aattaagaag aaactaagaa agtgggtaaa gtacgcactg | 6209 |
| ctgctcatga tggagtatta ctagtagtac attctctcta tttttttggg tagggatgat | 6269 |
| ggggagtagt gctagtagat tttttttctc ttttttttat agaaccgatg gggtaaataa | 6329 |
| atggaagctg ctgatatatg aattactgac tattgttctc tttgctttcc caatacttat | 6389 |
| attcttgata aactagaggc agggtttgaa atttcgaaat tggattttat gtcgggggtg | 6449 |
| aacgaaatta ccgaaaattt ctggccggaa ttatttgaaa atttgactaa attcacaaaa | 6509 |
| aaattgcaaa aaaactgaaa attttaggcg agatttgagc atgccggtgg agggcaaaat | 6569 |
| taccaaaatt tcggaaaatt cgaaccgaaa tttcaaaccc taactagagg atcataatca | 6629 |
| tatttatgga cagagggagc atgaatgaat atgaccgatg cttctagggt ttccttctac | 6689 |
| aagcatccta attagcttat tcaagttaga gtgcatccac tgcataactt ctttcgctgc | 6749 |
| ttcttcagct aattcagttg aacatatata accataaaac ctaacatttg aactgatgca | 6809 |
| <pre>g aaa tac agg atg caa ctg aag aaa tcg att cca aca aca agc aaa cac
  Lys Tyr Arg Met Gln Leu Lys Lys Ser Ile Pro Thr Thr Ser Lys His
       250                 255                 260</pre> | 6858 |
| <pre>gga gcg act ttg tca tcc acc gct ctc gac aaa aca caa gac cac cct
Gly Ala Thr Leu Ser Ser Thr Ala Leu Asp Lys Thr Gln Asp His Pro</pre> | 6906 |

-continued

| | | |
|---|---|---|
| Gly Ala Thr Leu Ser Ser Thr Ala Leu Asp Lys Thr Gln Asp His Pro<br>265 270 275 | | |
| tca aga tcg cag tat ttc aat caa gac gga tgc aag gaa atc atg gac<br>Ser Arg Ser Gln Tyr Phe Asn Gln Asp Gly Cys Lys Glu Ile Met Asp<br>280 285 290 295 | 6954 | |
| tac tct tta ccg aga gat gac ctc tca agt ggc tca gag tgc atg ctt<br>Tyr Ser Leu Pro Arg Asp Asp Leu Ser Ser Gly Ser Glu Cys Met Leu<br>300 305 310 | 7002 | |
| gaa gaa ctg aac gat tac tca tcc gaa ggt ttc caa gat ttc cga tgg<br>Glu Glu Leu Asn Asp Tyr Ser Ser Glu Gly Phe Gln Asp Phe Arg Trp<br>315 320 325 | 7050 | |
| gat tca gac aaa cag gaa tat gga cca tgt ttt tgg aat ttc tag<br>Asp Ser Asp Lys Gln Glu Tyr Gly Pro Cys Phe Trp Asn Phe<br>330 335 340 | 7095 | |
| gtagagaata taatgatccc atcatgtctc atgatccaca tccatatgtt gatacctgca | 7155 | |
| attgactttc tgaataagtg aacattacca catccatata tactcttgat gttcattgca | 7215 | |
| gaactaaact gacaacatac tgtacatagg ttgtctactc tatctagatg tgtcacatgc | 7275 | |
| aaagattatg ttgataacat tcatccaaat caatgtccat cctctcaatt atgggtgtgt | 7335 | |
| tgggggaagt tttagattct gagaagttgc tgaagataat acatgcatct aggtggcgac | 7395 | |
| aatctagaga tgtcgaggaa accaactttt ggcttatagt tcatttctg gattttacga | 7455 | |
| ctacaatttc ccaaaatatg gacaaaaagc tatatattcc tacatataag atccgtaatc | 7515 | |
| agaaaaaaaa acaatatatg gatcc | 7540 | |

<210> SEQ ID NO 8
<211> LENGTH: 1026
<212> TYPE: DNA
<213> ORGANISM: Oryza sativa
<220> FEATURE:
<221> NAME/KEY: CDS
<222> LOCATION: (1)..(1026)

<400> SEQUENCE: 8

| | |
|---|---|
| atg gat cac cga gag ctg tgg cct tat gga cta aga gtt ctg gtc atc<br>Met Asp His Arg Glu Leu Trp Pro Tyr Gly Leu Arg Val Leu Val Ile<br>1 5 10 15 | 48 |
| gat gac gac tgt tca tac ttg tca gtc atg gaa gat tta ctt ctg aag<br>Asp Asp Asp Cys Ser Tyr Leu Ser Val Met Glu Asp Leu Leu Leu Lys<br>20 25 30 | 96 |
| tgc agc tac aag gtt aca acg tat aag aac gtc aga gaa gct gtg cct<br>Cys Ser Tyr Lys Val Thr Thr Tyr Lys Asn Val Arg Glu Ala Val Pro<br>35 40 45 | 144 |
| ttc ata ttg gac aat cca caa ata gtt gac cta gta atc agt gat gcg<br>Phe Ile Leu Asp Asn Pro Gln Ile Val Asp Leu Val Ile Ser Asp Ala<br>50 55 60 | 192 |
| ttc ttt cct acc gaa gat ggt ttg ctc att ctg caa gaa gta acc tcc<br>Phe Phe Pro Thr Glu Asp Gly Leu Leu Ile Leu Gln Glu Val Thr Ser<br>65 70 75 80 | 240 |
| aag ttt ggc ata cct aca gtg att atg gct tca agt gga gac aca aat<br>Lys Phe Gly Ile Pro Thr Val Ile Met Ala Ser Ser Gly Asp Thr Asn<br>85 90 95 | 288 |
| aca gtg atg aaa tat gtt gca aat ggc gct ttt gat ttc ctg cta aaa<br>Thr Val Met Lys Tyr Val Ala Asn Gly Ala Phe Asp Phe Leu Leu Lys<br>100 105 110 | 336 |
| cct gtg agg atc gaa gag ctg agc aac att tgg cag cac ata ttc cga<br>Pro Val Arg Ile Glu Glu Leu Ser Asn Ile Trp Gln His Ile Phe Arg<br>115 120 125 | 384 |
| aag caa atg caa gat cac aag aac aat aac atg gtt gga aat ctc gaa | 432 |

```
Lys Gln Met Gln Asp His Lys Asn Asn Asn Met Val Gly Asn Leu Glu
            130                 135                 140 aaa ccc ggt cat cct cca tca ata tta gcc atg gct cgt gct act ccg      480
Lys Pro Gly His Pro Pro Ser Ile Leu Ala Met Ala Arg Ala Thr Pro
145                 150                 155                 160 gct acc acg aga tca acg gcc acc gaa gct tcg cta gcg cct cta gaa      528
Ala Thr Thr Arg Ser Thr Ala Thr Glu Ala Ser Leu Ala Pro Leu Glu
                165                 170                 175 aat gag gtg aga gat gac atg gtc aac tac aat ggc gag atc acg gac      576
Asn Glu Val Arg Asp Asp Met Val Asn Tyr Asn Gly Glu Ile Thr Asp
            180                 185                 190 ata cga gac ctc gga aag tcc agg ctg acc tgg acc acg cag ttg cac      624
Ile Arg Asp Leu Gly Lys Ser Arg Leu Thr Trp Thr Thr Gln Leu His
        195                 200                 205 cgt cag ttc att gca gca gtg aac cac ctc gga gaa gac aag gca gtt      672
Arg Gln Phe Ile Ala Ala Val Asn His Leu Gly Glu Asp Lys Ala Val
        210                 215                 220 cca aag aag ata cta ggg ata atg aag gtc aaa cat ttg aca aga gag      720
Pro Lys Lys Ile Leu Gly Ile Met Lys Val Lys His Leu Thr Arg Glu
225                 230                 235                 240 caa gtt gcc agt cat ctg cag aaa tac agg atg caa ctg aag aaa tcg      768
Gln Val Ala Ser His Leu Gln Lys Tyr Arg Met Gln Leu Lys Lys Ser
                245                 250                 255 att cca aca aca agc aaa cac gga gca act ttg tca tcc acc gct ctc      816
Ile Pro Thr Thr Ser Lys His Gly Ala Thr Leu Ser Ser Thr Ala Leu
            260                 265                 270 gac aaa aca caa gac cac cct tca aga tcg cag tat ttc aat caa gac      864
Asp Lys Thr Gln Asp His Pro Ser Arg Ser Gln Tyr Phe Asn Gln Asp
        275                 280                 285 gga tgc aag gaa atc atg gac tac tct tta ccg aga gat gac ctc tca      912
Gly Cys Lys Glu Ile Met Asp Tyr Ser Leu Pro Arg Asp Asp Leu Ser
        290                 295                 300 agt ggc tca gag tgc atg ctt gaa gaa ctg aac gat tac tca tcc gaa      960
Ser Gly Ser Glu Cys Met Leu Glu Glu Leu Asn Asp Tyr Ser Ser Glu
305                 310                 315                 320 ggt ttc caa gat ttc cga tgg gat tca gac aaa cag gaa tat gga cca     1008
Gly Phe Gln Asp Phe Arg Trp Asp Ser Asp Lys Gln Glu Tyr Gly Pro
                325                 330                 335 tgt ttt tgg aat ttc tag                                             1026
Cys Phe Trp Asn Phe
            340

<210> SEQ ID NO 9
<211> LENGTH: 341
<212> TYPE: PRT
<213> ORGANISM: Oryza sativa

<400> SEQUENCE: 9

Met Asp His Arg Glu Leu Trp Pro Tyr Gly Leu Arg Val Leu Val Ile
1               5                   10                  15

Asp Asp Asp Cys Ser Tyr Leu Ser Val Met Glu Asp Leu Leu Leu Lys
                20                  25                  30

Cys Ser Tyr Lys Val Thr Thr Tyr Lys Asn Val Arg Glu Ala Val Pro
            35                  40                  45

Phe Ile Leu Asp Asn Pro Gln Ile Val Asp Leu Val Ile Ser Asp Ala
        50                  55                  60

Phe Phe Pro Thr Glu Asp Gly Leu Leu Ile Leu Gln Glu Val Thr Ser
65                  70                  75                  80

Lys Phe Gly Ile Pro Thr Val Ile Met Ala Ser Ser Gly Asp Thr Asn
```

```
                85                  90                  95
Thr Val Met Lys Tyr Val Ala Asn Gly Ala Phe Asp Phe Leu Leu Lys
            100                 105                 110
Pro Val Arg Ile Glu Glu Leu Ser Asn Ile Trp Gln His Ile Phe Arg
        115                 120                 125
Lys Gln Met Gln Asp His Lys Asn Asn Asn Met Val Gly Asn Leu Glu
    130                 135                 140
Lys Pro Gly His Pro Pro Ser Ile Leu Ala Met Ala Arg Ala Thr Pro
145                 150                 155                 160
Ala Thr Thr Arg Ser Thr Ala Thr Glu Ala Ser Leu Ala Pro Leu Glu
                165                 170                 175
Asn Glu Val Arg Asp Asp Met Val Asn Tyr Asn Gly Glu Ile Thr Asp
            180                 185                 190
Ile Arg Asp Leu Gly Lys Ser Arg Leu Thr Trp Thr Gln Leu His
        195                 200                 205
Arg Gln Phe Ile Ala Ala Val Asn His Leu Gly Glu Asp Lys Ala Val
    210                 215                 220
Pro Lys Lys Ile Leu Gly Ile Met Lys Val Lys His Leu Thr Arg Glu
225                 230                 235                 240
Gln Val Ala Ser His Leu Gln Lys Tyr Arg Met Gln Leu Lys Lys Ser
                245                 250                 255
Ile Pro Thr Thr Ser Lys His Gly Ala Thr Leu Ser Ser Thr Ala Leu
            260                 265                 270
Asp Lys Thr Gln Asp His Pro Ser Arg Ser Gln Tyr Phe Asn Gln Asp
        275                 280                 285
Gly Cys Lys Glu Ile Met Asp Tyr Ser Leu Pro Arg Asp Asp Leu Ser
    290                 295                 300
Ser Gly Ser Glu Cys Met Leu Glu Glu Leu Asn Asp Tyr Ser Ser Glu
305                 310                 315                 320
Gly Phe Gln Asp Phe Arg Trp Asp Ser Asp Lys Gln Glu Tyr Gly Pro
                325                 330                 335
Cys Phe Trp Asn Phe
            340

<210> SEQ ID NO 10
<211> LENGTH: 7720
<212> TYPE: DNA
<213> ORGANISM: Oryza sativa
<220> FEATURE:
<223> OTHER INFORMATION: genomic DNA
<220> FEATURE:
<221> NAME/KEY: long TA repeats
<222> LOCATION: (1522)..(1722)
<223> OTHER INFORMATION: n means one or more TA repeats. The positions
      of CDS regions in the whole nucleotide sequence and the length of
      the whole nucleotide sequence may change, depending on the number
      of the TA repeats.
<220> FEATURE:
<221> NAME/KEY: CDS
<222> LOCATION: (2039)..(2147)
<220> FEATURE:
<221> NAME/KEY: CDS
<222> LOCATION: (3398)..(3550)
<220> FEATURE:
<221> NAME/KEY: CDS
<222> LOCATION: (5392)..(5793)
<220> FEATURE:
<221> NAME/KEY: CDS
<222> LOCATION: (5943)..(6019)
<220> FEATURE:
<221> NAME/KEY: CDS
<222> LOCATION: (6991)..(7275)
```

<400> SEQUENCE: 10

```
ggtacctatt tgttccatat ttttgctcga cattatctga gtttgtatcc atattcaaca      60
ctatccgtgt ttgatccgat tccaattata aaatatgggt taggatatgg aagggtaag     120
atccgaccga acccgacccg ttttcacccc tacacgtcgc taatctacac ttcgaggcaa    180
aaaaaaaaga gagtaacaaa tcaaactaca aaagcgcgca atcgcataca caataattaa    240
atttgtatct atcgtcacat atacaaataa aatttgatct tgcatatttg caccacaata    300
aggtaatacc tatgttttct acttttttaga aaatttatta ataacttttt ttagataatt   360
tatgaataac tatttggacc acaggaaata gacaacgtag tacgacacat tctttcctag    420
gtcttatgta cgcatgattg tgtgtatatt ctcgcctacg ccgacgacgg tgaccggtgc    480
atatgttccc agccgtcctc cgccgcgcat tgcggttgtg gaggaaggga gctccacgtc    540
tcgccatggc cgtccacaac ctgagttaga tctctagcta cctgatcccc aaaccctctc    600
aaaaagatgt atattcttcc tagcactctg gcccctggat tagctcaaaa attcctcata    660
tatatgctgg ctagctagct gatagtatat actactcata acccattctt cttccttacc    720
tagctagcta gcaaacactg aagctgggag ctctggctat atgtccatat atatatatat    780
actacatcat tgctatagct agctagctgg aggaggaaca ttcatactta attctagtta    840
cttggagtga gtttaaaaca ctgaattagg tgaaattgac cggtggccgc tgactgctgg    900
caggctagct ttggtgatta ttaattatc tgtcggagta agtcttatac ttgatattac     960
atgcatggaa gaaggtatat atgtctacgc caacattcat gtacttagtc ctctactatt   1020
tctacatagt taattacaac ccaccattaa ctgtattaat tacttagaac tctcacattt   1080
aaccacgtca tgatcatatc aacggtgtta tccatcaatt gaggtgtgtc gtctatgaga   1140
tatcagcaat taattaagat caacatttct cagcaaagga gctttaaaac cctgctgcaa   1200
atatgcaggg gtacgtatcc aaatatatca tataccctg tcgtatatag tatttacatg    1260
tagttattga tgatgataga ttgctcatgc atggaggtga ttatttcttg tgtgtttggt   1320
ttgttttgcc tggaaatagc tatagctttg cacatatagc tgcttaaata ttcttgaatg   1380
cagacatacg agttttcgat atatactcag atatattagt acaatattat tatttgtatg   1440
catatcatca gtgactcgat tgatatttga agatatatac ttatataaaa atgcaaggat   1500
atatgcatga agaacatgtc catatatata tatatatata tatatatata tatatatata   1560
tatatatata tatatatata tatatatata tatatatata tatatatata tatatatata   1620
tatatatata tatatataca tatatatata tatatatata tatatatata tatatatata   1680
tatatatata tatatatata tatatatata tatatatata tnagagagag agagagagag   1740
agagagagag agagatctgt gtctagcttg cactacacca tatatatata taacctacct   1800
tagccaaagg agtcagttat taactgtagt tagcattatt gttgaattaa tgctatacct   1860
cattaactat atatggtgca cgcgcattcc atgcatcatg catgtttatt actcgtcata   1920
tattatatac gatgtaaaca caaagtacaa ttgattatat tattgttaat tatttttta    1980
aaaacggaga agcagatgta gtcgttaatt tttgttttct cctaattagg ttataata     2038
atg gat cac cga gag ctg tgg cct tat gga cta aga gtt ctg gtc atc     2086
Met Asp His Arg Glu Leu Trp Pro Tyr Gly Leu Arg Val Leu Val Ile
 1               5                  10                  15
gat gac gac tgt tca tac ttg tca gtc atg gaa gat tta ctt ctg aag     2134
Asp Asp Asp Cys Ser Tyr Leu Ser Val Met Glu Asp Leu Leu Leu Lys
            20                  25                  30
```

```
tgc agc tac aag g gtaaaatac catctataca agacacataa ttaattaaca          2186
Cys Ser Tyr Lys
        35 aaatctaact atctagcttg gcatatatag tgatcgaata tattgatgcg aattaagatt     2246 atataagatt atacatataa aatattgagt ttttctggat taaatagaag atgcatacag     2306 aagttacaaa cacgcaccac tacacacgtg tccatgcaca ctaatgtgtc tcctaatata     2366 tacatgctca gatacgctca gatagacaga tcagatcaat ggcaaatctt tgacctcact     2426 aaaatcctat tggaagtatg tgcataaaat ttgtaaataa aatttgtata agatcattaa     2486 tttttctact atttaagttc agtcagtttc acatgcataa tacatgataa tcctatatta     2546 tgtatatata tcattccatg cttactttaa ccaaattttc cctctacctt ggtgtagcca     2606 atgcatcata tagttataat atgttatgaa tacataaata tatagcagaa tttatgttca     2666 ttgtcacata aaatgtgttt gcatgattct tattattaaa ataaatattt ggtaatgtgt     2726 ttcagctaac aggcacatgg aatatagtca agatgatca gctctgtggt tggactgcca      2786 tttgctttga agaagctaca aaaatttaat taattttgaa aatgaaataa aacatgcggg     2846 agttctatat agtgtatata ccttaaaata attcttttct ttcttcccat ttagtttgtc     2906 aaattagact gcaagtagta attaaatcga agtcttggag ggtagtgcag aacatatatt     2966 aagaacaaag gtatacttta attatatatc ctcaccttgc agttgcggtt tctagggtta     3026 gcatatattt tgtgaggtgt caactcagat attgtgatga caaattaacc tataaatttt     3086 ctccatatgt ttttattcaa tgggcgatcc atactccata aaatgcatat taattaattt     3146 gtaatgaaaa ccgggaaaag ttgtgttcgt atatatacca agaatcttgc aagaaagtga     3206 ttgtatgtag taacatttcc atacacacat gaagttacac acacacacac acacatatta     3266 tatatatata tatatatata tatatagtct aacgtcaaaa atgaaattct tctagatata     3326 tcttacaaat attcgatatt ggcctcattt tctttgtgat gtatgtacct tatattagta     3386 ttctcttgta g tt aca acg tat aag aac gtc aga gaa gct gtg cct ttc       3435
            Val Thr Thr Tyr Lys Asn Val Arg Glu Ala Val Pro Phe
                    40                  45 ata ttg gac aat cca caa ata gtt gac cta gta atc agt gat gcg ttc       3483
Ile Leu Asp Asn Pro Gln Ile Val Asp Leu Val Ile Ser Asp Ala Phe
 50              55                  60                  65 ttt cct acc gaa gat ggt ttg ctc att ctg caa gaa gta acc tcc aag       3531
Phe Pro Thr Glu Asp Gly Leu Leu Ile Leu Gln Glu Val Thr Ser Lys
                 70                  75                  80 ttt ggc ata cct aca gtg a gtaagtaat ttatttatta tctccttaca             3579
Phe Gly Ile Pro Thr Val
             85 cattcttact agtttatatg gattacacgc cttaacttat gcgtgcgtgt gtgcttgagg     3639 aactaggtca aatatgcact aatatataat aagctactca ctccgtctca aaatataact     3699 actttcgcta cgcgcgggtc aggtcatctg tgatgggccc aaaccgtacc tctgacaggt     3759 tcggccctca tcagagatta gtggtcagcc tactcacctc tgacgggccg ttagaaatgg     3819 gtcgtcacag gtgactcact tgtgatgtgt ggctctttcc aacatgtcag aggtgactgt     3879 caccttgac gggttgtatt ttatcactta tcacaggtgt gaaaaaacaa cccaaaagaa      3939 aaagcaaaag ccctcagccc caagctcacg ccaagagcat aacacaacat ctttgcattt     3999 tattggcaga tctgataaca tccaagaaaa aactacagat gaaacaaaag atgtatgata     4059 catatcaaac ttgagtaaca atatacatca cacaagtaat gatctccatc ctaacaaact     4119 acacatccac acaagtaaca aagaatatgg cccaatctga aatttggcag tgaacatttg     4179
```

-continued

```
caagatatga aatcaagaac aacctacagg agtgtcaagg tcagggaggc cgccgtgctc    4239
cccctccacc cctgtcagat ctacccacca actccaccac cagatctgcc aatcctccag    4299
ggtcagagag ctagatccac cgctcgagga gagcctagat ccgcacttgt gatagggacg    4359
gctaccattg ctttggactg agaagacga ggaaatggca tcaatgatcg gggaggctag     4419
atctgcaccc gaggaggcag ctggtgcttg agggtagagg agacagcggc caacagtcgg    4479
atcgatccat gtccccgac cttgtggagg ctagatccca cggtcgccgg atgctggcgg     4539
agatggggga gcccgggctc gggggagagg ccggctccgg tggccggcgg ttgggtgata    4599
aaggaggagg cggccaacag tcagggaga ggccgcggcg gccggtgatt ggggaagga      4659 ggacgcaacg gctggagatc ggggaaagga ggaggcggta gccgaatcca catcctggag    4719
gcaagatccg gcgaccggtg atcaggaggc ggttagggga agagagtttg agatatgggg    4779
ataaggatga gagggagaaa gtgagcagat gtgaggagaa gaaagaagag agaccggagg    4839
atgggaggag atgggaaggg agttgggccg tacacatggg gattggggga ttttcctta    4899 ttttaaatta tcattgacga gcataagaat ttaacacgtt agatatgagg tatcacatcc    4959
tgtgatgagg tgcaaactca acacccgtca cagatagaag gtcatatatg acgggcctat    5019
atgtgggccc gtcaaagatg ttatgtgtcg agtcctcata aatgtccgta agatgagttt    5079
ttacttgtga cgagccatcc ctttgaaccc catctacaac tggctatagt tcaaccctat    5139
cagaaataat atctttcgtg acgagacatt ggcctgtcac agatatgccg tcacaatggg    5199
ctgctctagt gaagtgttcg agaattcaaa ttcgtctcaa ccaatcacaa tcatttaatt    5259
tattcaccta ttttttttatc tcaaccaatc gcaatcattt tttataaat agtaatattc    5319 tgagacaaaa ggatcggagt acaccctaat aagtttactc acaaggaaac tttatatatg    5379
ttttttaact ag tt atg gct tca agt gga gac aca aat aca gtg atg aaa    5429
              Ile Met Ala Ser Ser Gly Asp Thr Asn Thr Val Met Lys
                      90              95                 100 tat gtt gca aat ggc gct ttt gat ttc ctg cta aaa cct gtg agg atc     5477
Tyr Val Ala Asn Gly Ala Phe Asp Phe Leu Leu Lys Pro Val Arg Ile
            105                 110                 115 gaa gag ctg agc aac att tgg cag cac ata ttc cga aag caa atg caa    5525
Glu Glu Leu Ser Asn Ile Trp Gln His Ile Phe Arg Lys Gln Met Gln
        120                 125                 130 gat cac aag aac aat aac atg gtt gga aat ctc gaa aaa ccc ggt cat    5573
Asp His Lys Asn Asn Asn Met Val Gly Asn Leu Glu Lys Pro Gly His
        135                 140                 145 cct cca tca ata tta gcc atg gct cgt gct act ccg gct acc acg aga    5621
Pro Pro Ser Ile Leu Ala Met Ala Arg Ala Thr Pro Ala Thr Thr Arg
    150                 155                 160 tca acg gcc acc gaa gct tcg cta gcg cct cta gaa aat gag gtg aga    5669
Ser Thr Ala Thr Glu Ala Ser Leu Ala Pro Leu Glu Asn Glu Val Arg
165                 170                 175                 180 gat gac atg gtc aac tac aat ggc gag atc acg gac ata cga gac ctc    5717
Asp Asp Met Val Asn Tyr Asn Gly Glu Ile Thr Asp Ile Arg Asp Leu
                185                 190                 195 gga aag tcc agg ctg acc tgg acc acg cag ttg cac cgt cag ttc att    5765
Gly Lys Ser Arg Leu Thr Trp Thr Thr Gln Leu His Arg Gln Phe Ile
            200                 205                 210 gca gca gtg aac cac ctc aga gaa gac a gtgagtgat caaattaaac          5812
Ala Ala Val Asn His Leu Arg Glu Asp
        215                 220 ttctttgcag taccatttca atcactttc atatgtatac atgcgtgtat acattaattt    5872
```

```
taatttacta gtatatatgt atttcctagc ttgttttaag atgtggtaat tatgtgtaat        5932
ttatttgcag ag gca gtt cca aag aag ata cta ggg ata atg aag gtc aaa       5983
           Lys Ala Val Pro Lys Lys Ile Leu Gly Ile Met Lys Val Lys
                   225                 230                 235 cat ttg aca aga gag caa gtt gcc agt cat ctg cag gtaatatttc              6029
His Leu Thr Arg Glu Gln Val Ala Ser His Leu Gln
                240                 245 agtggctcat tgcaagatga aagcaaaacc tatcatgttt ttcctttcaa gatttcttta       6089
cgataaatta gaccatatgc aagatatata caagggcaaa ttccctccag agttttttaga      6149 aaacactttc caatgtataa tatgtaaaaa tgtgttgtcc atgttacaat gattcttaat       6209
tatactactt tcacaattgt acatataaat tagcctaata ctactcatac atatgtatca       6269
ggtacacatt gtaagtttat atatttgcat cactctaatg tactccctag ctctgtccat       6329
gaatacaagg gattataccc aattaagaag aaactaagaa agtgggtaaa gtacgcactg       6389
ctgctcatga tggagtatta ctagtagtac attctctcta ttttttttggg tagggatgat      6449 ggggagtagt gctagtagat ttttttttctc tttttttttat agaaccgatg gggtaaataa     6509
atggaagctg ctgatatatg aattactgac tattgttctc tttgctttcc caatacttat       6569
attcttgata aactagaggc agggtttgaa atttcgaaat tggattttat gtcgggggtg       6629
aacgaaatta ccgaaaattt ctggccggaa ttatttgaaa atttgactaa attcacaaaa       6689
aaattgcaaa aaaactgaaa atttttaggcg agatttgagc atgccggtgg agggcaaaat      6749
taccaaaatt tcggaaaatt cgaaccgaaa tttcaaaccc taactagagg atcataatca      6809
tatttatgga cagagggagc atgaatgaat atgaccgatg cttctagggt ttccttctac       6869
aagcatccta attagcttat tcaagttaga gtgcatccac tgcataactt ctttcgctgc      6929
ttcttcagct aattcagttg aacatatata accataaaac ctaacatttg aactgatgca      6989 g aaa tac agg atg caa ctg aag aaa tcg att cca aca aca agc aaa cac      7038
  Lys Tyr Arg Met Gln Leu Lys Lys Ser Ile Pro Thr Thr Ser Lys His
          250                 255                 260 gga gcg act ttg tca tcc acc gct ctc gac aaa aca caa gac cac cct        7086
Gly Ala Thr Leu Ser Ser Thr Ala Leu Asp Lys Thr Gln Asp His Pro
265                 270                 275 tca aga tcg cag tat ttc aat caa gac gga tgc aag gaa atc atg gac        7134
Ser Arg Ser Gln Tyr Phe Asn Gln Asp Gly Cys Lys Glu Ile Met Asp
280                 285                 290                 295 tac tct tta ccg aga gat gac ctc tca agt ggc tca gag tgc atg ctt        7182
Tyr Ser Leu Pro Arg Asp Asp Leu Ser Ser Gly Ser Glu Cys Met Leu
            300                 305                 310 gaa gaa ctg aac gat tac tca tcc gaa ggt ttc caa gat ttc cga tgg        7230
Glu Glu Leu Asn Asp Tyr Ser Ser Glu Gly Phe Gln Asp Phe Arg Trp
                315                 320                 325 gat tca gac aaa cag gaa tat gga cca tgt ttt tgg aat ttc tag            7275
Asp Ser Asp Lys Gln Glu Tyr Gly Pro Cys Phe Trp Asn Phe
                    330                 335                 340 gtagagaata taatgatccc atcatgtctc atgatccaca tccatatgtt gatacctgca      7335
attgactttc tgaataagtg aacattacca catccatata tactcttgat gttcattgca      7395
gaactaaact gacaacatac tgtacatagg ttgtctactc tatctagatg tgtcacatgc      7455
aaagattatg ttgataacat tcatccaaat caatgtccat cctctcaatt atgggtgtgt      7515
ttggggaagt tttagattct gagaagttgc tgaagataat acatgcatct aggtggcgac      7575
aatctagaga tgtcgaggaa accaactttt ggcttatagt tcattttctg gattttacga      7635
ctacaatttc ccaaaatatg gacaaaaagc tatatattcc tacatataag atccgtaatc      7695
```

```
agaaaaaaaa acaatatatg gatcc                                          7720

<210> SEQ ID NO 11
<211> LENGTH: 1026
<212> TYPE: DNA
<213> ORGANISM: Oryza sativa
<220> FEATURE:
<221> NAME/KEY: CDS
<222> LOCATION: (1)..(1026)

<400> SEQUENCE: 11 atg gat cac cga gag ctg tgg cct tat gga cta aga gtt ctg gtc atc       48
Met Asp His Arg Glu Leu Trp Pro Tyr Gly Leu Arg Val Leu Val Ile
  1               5                  10                  15 gat gac gac tgt tca tac ttg tca gtc atg gaa gat tta ctt ctg aag       96
Asp Asp Asp Cys Ser Tyr Leu Ser Val Met Glu Asp Leu Leu Leu Lys
             20                  25                  30 tgc agc tac aag gtt aca acg tat aag aac gtc aga gaa gct gtg cct      144
Cys Ser Tyr Lys Val Thr Thr Tyr Lys Asn Val Arg Glu Ala Val Pro
         35                  40                  45 ttc ata ttg gac aat cca caa ata gtt gac cta gta atc agt gat gcg      192
Phe Ile Leu Asp Asn Pro Gln Ile Val Asp Leu Val Ile Ser Asp Ala
     50                  55                  60 ttc ttt cct acc gaa gat ggt ttg ctc att ctg caa gaa gta acc tcc      240
Phe Phe Pro Thr Glu Asp Gly Leu Leu Ile Leu Gln Glu Val Thr Ser
 65                  70                  75                  80 aag ttt ggc ata cct aca gtg att atg gct tca agt gga gac aca aat      288
Lys Phe Gly Ile Pro Thr Val Ile Met Ala Ser Ser Gly Asp Thr Asn
                 85                  90                  95 aca gtg atg aaa tat gtt gca aat ggc gct ttt gat ttc ctg cta aaa      336
Thr Val Met Lys Tyr Val Ala Asn Gly Ala Phe Asp Phe Leu Leu Lys
            100                 105                 110 cct gtg agg atc gaa gag ctg agc aac att tgg cag cac ata ttc cga      384
Pro Val Arg Ile Glu Glu Leu Ser Asn Ile Trp Gln His Ile Phe Arg
        115                 120                 125 aag caa atg caa gat cac aag aac aat aac atg gtt gga aat ctc gaa      432
Lys Gln Met Gln Asp His Lys Asn Asn Asn Met Val Gly Asn Leu Glu
    130                 135                 140 aaa ccc ggt cat cct cca tca ata tta gcc atg gct cgt gct act ccg      480
Lys Pro Gly His Pro Pro Ser Ile Leu Ala Met Ala Arg Ala Thr Pro
145                 150                 155                 160 gct acc acg aga tca acg gcc acc gaa gct tcg cta gcg cct cta gaa      528
Ala Thr Thr Arg Ser Thr Ala Thr Glu Ala Ser Leu Ala Pro Leu Glu
                165                 170                 175 aat gag gtg aga gat gac atg gtc aac tac aat ggc gag atc acg gac      576
Asn Glu Val Arg Asp Asp Met Val Asn Tyr Asn Gly Glu Ile Thr Asp
            180                 185                 190 ata cga gac ctc gga aag tcc agg ctg acc tgg acc acg cag ttg cac      624
Ile Arg Asp Leu Gly Lys Ser Arg Leu Thr Trp Thr Thr Gln Leu His
        195                 200                 205 cgt cag ttc att gca gca gtg aac cac ctc aga gaa gac aag gca gtt      672
Arg Gln Phe Ile Ala Ala Val Asn His Leu Arg Glu Asp Lys Ala Val
    210                 215                 220 cca aag aag ata cta ggg ata atg aag gtc aaa cat ttg aca aga gag      720
Pro Lys Lys Ile Leu Gly Ile Met Lys Val Lys His Leu Thr Arg Glu
225                 230                 235                 240 caa gtt gcc agt cat ctg cag aaa tac agg atg caa ctg aag aaa tcg      768
Gln Val Ala Ser His Leu Gln Lys Tyr Arg Met Gln Leu Lys Lys Ser
                245                 250                 255 att cca aca aca agc aaa cac gga gcg act ttg tca tcc acc gct ctc      816
Ile Pro Thr Thr Ser Lys His Gly Ala Thr Leu Ser Ser Thr Ala Leu
```

```
Ile Pro Thr Thr Ser Lys His Gly Ala Thr Leu Ser Ser Thr Ala Leu
            260                 265                 270 gac aaa aca caa gac cac cct tca aga tcg cag tat ttc aat caa gac        864
Asp Lys Thr Gln Asp His Pro Ser Arg Ser Gln Tyr Phe Asn Gln Asp
        275                 280                 285 gga tgc aag gaa atc atg gac tac tct tta ccg aga gat gac ctc tca        912
Gly Cys Lys Glu Ile Met Asp Tyr Ser Leu Pro Arg Asp Asp Leu Ser
290                 295                 300 agt ggc tca gag tgc atg ctt gaa gaa ctg aac gat tac tca tcc gaa        960
Ser Gly Ser Glu Cys Met Leu Glu Glu Leu Asn Asp Tyr Ser Ser Glu
305                 310                 315                 320 ggt ttc caa gat ttc cga tgg gat tca gac aaa cag gaa tat gga cca       1008
Gly Phe Gln Asp Phe Arg Trp Asp Ser Asp Lys Gln Glu Tyr Gly Pro
                325                 330                 335 tgt ttt tgg aat ttc tag                                               1026
Cys Phe Trp Asn Phe
                340
```

<210> SEQ ID NO 12
<211> LENGTH: 341
<212> TYPE: PRT
<213> ORGANISM: Oryza sativa

<400> SEQUENCE: 12

```
Met Asp His Arg Glu Leu Trp Pro Tyr Gly Leu Arg Val Leu Val Ile
1               5                   10                  15

Asp Asp Asp Cys Ser Tyr Leu Ser Val Met Glu Asp Leu Leu Leu Lys
            20                  25                  30

Cys Ser Tyr Lys Val Thr Thr Tyr Lys Asn Val Arg Glu Ala Val Pro
        35                  40                  45

Phe Ile Leu Asp Asn Pro Gln Ile Val Asp Leu Val Ile Ser Asp Ala
    50                  55                  60

Phe Phe Pro Thr Glu Asp Gly Leu Leu Ile Leu Gln Glu Val Thr Ser
65                  70                  75                  80

Lys Phe Gly Ile Pro Thr Val Ile Met Ala Ser Ser Gly Asp Thr Asn
                85                  90                  95

Thr Val Met Lys Tyr Val Ala Asn Gly Ala Phe Asp Phe Leu Leu Lys
            100                 105                 110

Pro Val Arg Ile Glu Glu Leu Ser Asn Ile Trp Gln His Ile Phe Arg
        115                 120                 125

Lys Gln Met Gln Asp His Lys Asn Asn Asn Met Val Gly Asn Leu Glu
    130                 135                 140

Lys Pro Gly His Pro Pro Ser Ile Leu Ala Met Ala Arg Ala Thr Pro
145                 150                 155                 160

Ala Thr Thr Arg Ser Thr Ala Thr Glu Ala Ser Leu Ala Pro Leu Glu
                165                 170                 175

Asn Glu Val Arg Asp Asp Met Val Asn Tyr Asn Gly Glu Ile Thr Asp
            180                 185                 190

Ile Arg Asp Leu Gly Lys Ser Arg Leu Thr Trp Thr Thr Gln Leu His
        195                 200                 205

Arg Gln Phe Ile Ala Ala Val Asn His Leu Arg Glu Asp Lys Ala Val
    210                 215                 220

Pro Lys Lys Ile Leu Gly Ile Met Lys Val Lys His Leu Thr Arg Glu
225                 230                 235                 240

Gln Val Ala Ser His Leu Gln Lys Tyr Arg Met Gln Leu Lys Lys Ser
                245                 250                 255
```

```
Ile Pro Thr Thr Ser Lys His Gly Ala Thr Leu Ser Ser Thr Ala Leu
            260                 265                 270

Asp Lys Thr Gln Asp His Pro Ser Arg Ser Gln Tyr Phe Asn Gln Asp
        275                 280                 285

Gly Cys Lys Glu Ile Met Asp Tyr Ser Leu Pro Arg Asp Asp Leu Ser
    290                 295                 300

Ser Gly Ser Glu Cys Met Leu Glu Leu Asn Asp Tyr Ser Ser Glu
305                 310                 315                 320

Gly Phe Gln Asp Phe Arg Trp Asp Ser Asp Lys Gln Glu Tyr Gly Pro
                325                 330                 335

Cys Phe Trp Asn Phe
            340

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13
ccaatgaagg gtaagtatcg                                              20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 14
tgtgcttaag atacacggta gttca                                        25

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 15
ctgcagcttc caccatggca                                              20

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 16
caagggtgca ttcattgcac ctcctctagc catggcctaa tgatgca                47

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence
```

<400> SEQUENCE: 17
acgctgcaac aaagagcaga                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 18
ttgttgacga aagcccattg                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 19
ggagatcatg ctcacggatg                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 20
caagcaaaca cggagcgact                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 21
ccttgcatcc gtcttgattg                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 22
gggcaaattc cctccagagt                                              20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 23

```
tttggatacg tacccctgca t                                              21
```

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 24

```
gcgcaatcgc atacacaata a                                              21
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 25

```
gagcccgagc ccatgtatag                                                20
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 26

```
tggctaagat ggagggacga                                                20
```

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 27

```
attgggccaa actgcaagat                                                20
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 28

```
acgagcctaa tgggggagat                                                20
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 29

```
-continued gagatcaacg gccaccgaag                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 30
gtcgagagcg gtggatgaca                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 31
tggatcaccg agagctgtgg                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 32
atttccttgc atccgtcttg                                               20
```

The invention claimed:

1. An isolated A DNA according to (a) or (b) below, wherein said DNA encodes a plant-derived protein that functions to promote plant flowering:
   (a) a DNA encoding a protein comprising the amino acid sequence of SEQ ID NO:6;
   (b) a DNA consisting of the nucleotide sequence of SEQ ID NO:4 or 5.

2. A vector comprising the DNA of claim 1.

3. A transformed plant cell comprising the DNA of claim 1.

4. A transgenic plant comprising the transformed plant cell of claim 3.

5. A transgenic plant that is a progeny or a clone of the transgenic plant of claim 4 and wherein the progeny or clone comprise an isolated DNA encoding a protein comprising the amino acid sequence of SEQ ID NO:6 or an isolated DNA consisting of the nucleotide sequence of SEQ ID NO:4 or 5.

6. A breeding material of the transgenic plant of claim 4 and wherein the breeding material comprises an isolated DNA encoding a protein comprising the amino acid sequence of SEQ ID NO:6 or an isolated DNA consisting of the nucleotide sequence of SEQ ID NO:4 or 5.

7. A method for producing a transgenic plant, comprising the steps of introducing the DNA of claim 1 into a plant cell, and regenerating a plant from said plant cell.

8. A method for promoting plant flowering, comprising expressing the DNA of claim 1 in plant cells.

9. The method of claim 8, wherein the plant is rice.

10. A transformed plant cell comprising the vector of claim 2.

11. A transgenic plant comprising the transformed plant cell of claim 10.

12. A transgenic plant that is a progeny or a clone of the transgenic plant of claim 11 and wherein the progeny or clone comprise an isolated DNA encoding a protein comprising the amino acid sequence of SEQ ID NO:6 or an isolated DNA consisting of the nucleotide sequence of SEQ ID NO:4 or 5.

13. A breeding material of the transgenic plant of claim 11 and wherein the breeding material comprises an isolated DNA encoding a protein comprising the amino acid sequence of SEQ ID NO:6 or an isolated DNA consisting of the nucleotide sequence of SEQ ID NO:4 or 5.

14. A breeding material of the transgenic plant of claim 12 and wherein the breeding material comprises an isolated DNA encoding a protein comprising the amino acid sequence of SEQ ID NO:6 or an isolated DNA consisting of the nucleotide sequence of SEQ ID NO:4 or 5.

15. A method for producing a transgenic plant, comprising the steps of introducing the vector of claim 2 into a plant cell, and regenerating a plant from said plant cell.

16. A breeding material of the transgenic plant of claim 5 and wherein the breeding material comprises an isolated DNA encoding a protein comprising the amino acid sequence of SEQ ID NO:6 or an isolated DNA consisting of the nucleotide sequence of SEQ ID NO:4 or 5.

* * * * *

UNITED STATES PATENT AND TRADEMARK OFFICE
CERTIFICATE OF CORRECTION

| | | |
|---|---|---|
| PATENT NO. | : 7,361,805 B2 | Page 1 of 1 |
| APPLICATION NO. | : 10/515481 | |
| DATED | : April 22, 2008 | |
| INVENTOR(S) | : Yano et al. | |

It is certified that error appears in the above-identified patent and that said Letters Patent is hereby corrected as shown below:

In col. 75, line 39, claim 1, please delete "A DNA" and replace with --DNA--.

Signed and Sealed this

Fifteenth Day of July, 2008

JON W. DUDAS
*Director of the United States Patent and Trademark Office*